United States Patent [19]
Sholder

[11] Patent Number: 5,653,738
[45] Date of Patent: Aug. 5, 1997

[54] DDI PACING WITH PROTECTION AGAINST INDUCTION OF A PACEMAKER MEDICATED RETROGRADE RHYTHM

[75] Inventor: Jason A. Sholder, Beverly Hills, Calif.

[73] Assignee: Pacesetter, Inc., Sylmar, Calif.

[21] Appl. No.: 646,183

[22] Filed: May 7, 1996

Related U.S. Application Data

[63] Continuation-in-part of Ser. No. 372,626, Jan. 13, 1995, abandoned.

[51] Int. Cl.[6] .................................................. A61N 1/365
[52] U.S. Cl. .................................................. 607/14
[58] Field of Search ........................ 607/14, 15; 128/697, 128/705

[56] References Cited

U.S. PATENT DOCUMENTS

| | | | |
|---|---|---|---|
| 4,788,980 | 12/1988 | Mann et al. . | |
| 5,097,832 | 3/1992 | Buchanan . | |
| 5,247,929 | 9/1993 | Stoop et al. | 607/14 |
| 5,273,035 | 12/1993 | Markowitz et al. | 607/14 |
| 5,423,868 | 6/1995 | Nappholz et al. | 607/14 |

FOREIGN PATENT DOCUMENTS

0308535A1  3/1989  European Pat. Off. .

Primary Examiner—Jeffrey R. Jastrzab

[57] ABSTRACT

A DDI pacemaker detects when a pacemaker mediated retrograde rhythm (PMRR) occurs, and automatically alters the DDI operation to terminate the PMRR. The PMRR is detected by measuring the P-to-V time interval in a DDI pacing cycle that terminates in the generation of a ventricular stimulation pulse (V-pulse). A PMRR is presumed to be present whenever the measured P-to-V interval exceeds a prescribed time interval, or whenever a programmed number of consecutive P-to-V time intervals, e.g., ten, are greater than the prescribed time interval. Once a PMRR is detected, the pacemaker automatically extends the post-ventricular atrial refractory period (PVARP) of the pacemaker to block any retrograde P-waves that may be occurring as part of the PMRR. As soon as the extended PVARP terminates, an alert time interval, $T_{ALERT}$, begins that is selected to be of sufficient length to allow atrial tissue to repolarize and/or to detect a normal P-wave. If a P-wave is not sensed during the $T_{ALERT}$ interval, which will normally be the case in the presence of a PMRR, an atrial stimulation pulse (A-pulse) is generated that effectively prevents the next ventricular event from triggering a retrograde P-wave, thereby terminating the PMRR.

31 Claims, 9 Drawing Sheets

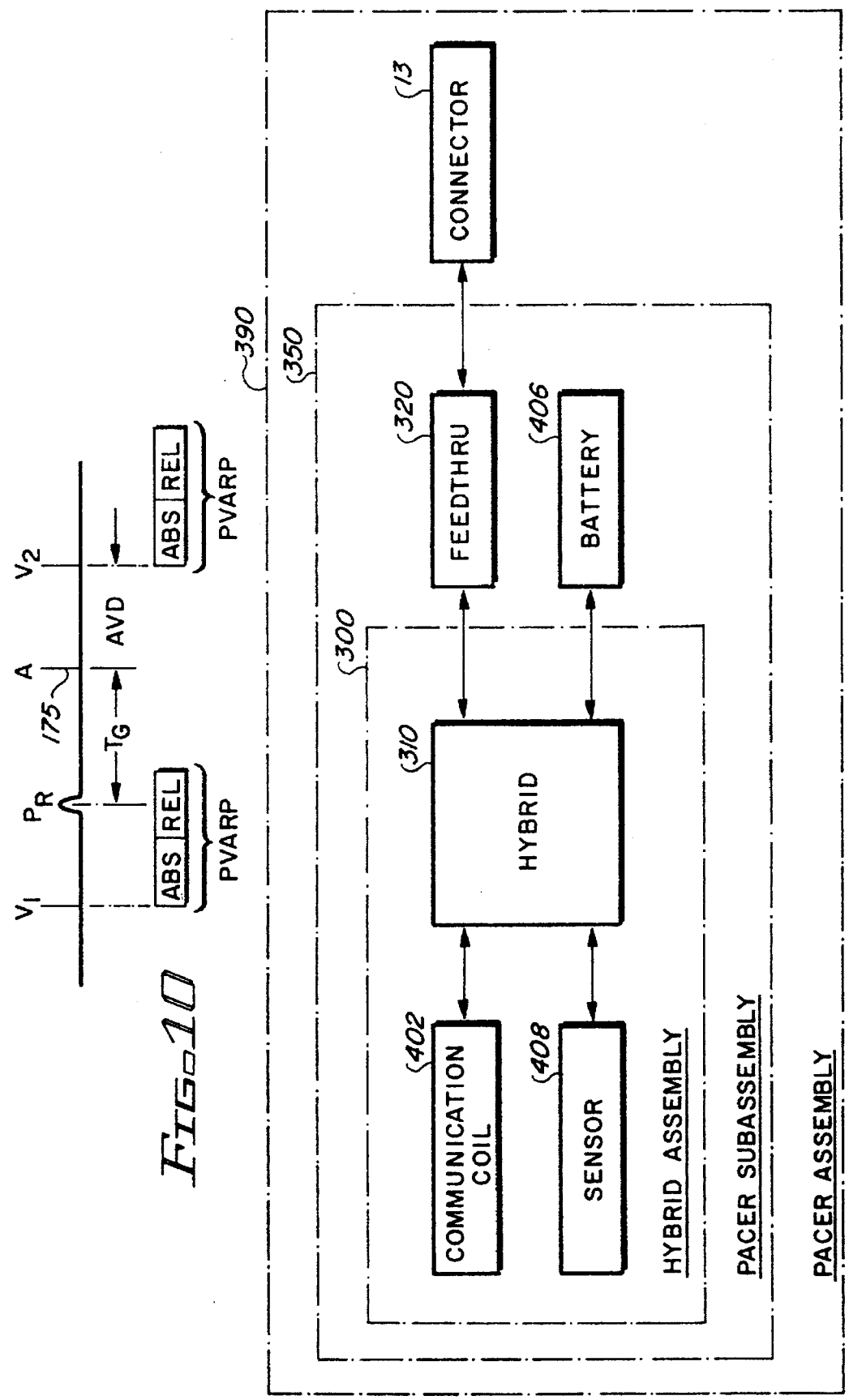

DDI PACING WITH PROTECTION AGAINST INDUCTION OF A PACEMAKER MEDICATED RETROGRADE RHYTHM

The present application is a continuation in part of application Ser. No. 08/372,626, filed Jan. 13, 1995 now abandoned.

BACKGROUND OF THE INVENTION

FIELD OF THE INVENTION

The present invention relates to implantable medical devices and methods, and more particularly to a dual-chamber implantable pacemaker or pacemaker system having enhanced behavior adapted to prevent a pacemaker mediated retrograde rhythm (PMRR) when operating in the DDI mode.

The basic function of the heart is to pump (circulate) blood throughout the body. The blood serves as a medium for delivering oxygen and nutrients to the various tissues while removing waste products and carbon dioxide. The heart is divided into four chambers comprised of two atria and two ventricles. The atria are the collecting chambers holding the blood which returns to the heart until the ventricles are ready to receive this blood. The ventricles are the primary pumping chambers. The pumping function of the heart is achieved by a coordinated contraction of the muscular walls of the atria and the ventricles.

The atria are more than simple collecting chambers. The atria contain the heart's own (natural, native or intrinsic) pacemaker that controls the rate at which the heart beats or contracts. In addition, the atrial contraction helps to fill the ventricle, further contributing to optimal filling and thus maximizing the amount of blood which the heart is able to pump with each contraction. Thus, atrial contraction is followed after a short period of time (normally 120 to 200 ms) by ventricular contraction.

The period of cardiac contraction during which the heart actively ejects the blood into the arterial blood vessels is called systole. The period of cardiac relaxation during which the chambers are being filled with blood is called diastole. Atrial and ventricular systole are sequenced allowing the atrial contraction to help optimally fill the ventricle. This is termed AV synchrony.

A cardiac cycle comprises one sequence of systole and diastole. It can be detected by counting the patient's pulse rate. It is also reflected by the cardiac rhythm as recorded by an electrocardiogram (ECG) or electrogram (EGM). The ECG is a recording of the electrical activity of the heart as seen using surface electrodes placed on the surface of the body. The EGM is a recording of the electrical activity of the heart as seen using electrodes placed within the heart. The electrical activity refers to the cardiac depolarization in either the atrium and/or ventricle. In general, on the ECG or EGM, the atrial depolarization is represented by a P-wave, while the ventricular depolarization is represented by a QRS complex, sometimes abbreviated as an "R-wave". The electrical depolarization triggers or initiates the active muscular contraction. Once the cardiac cells are depolarized, they must repolarize in order for the next depolarization and contraction to occur. Ventricular repolarization is represented by the T-wave. Atrial repolarization is rarely seen on an ECG or EGM as it occurs at virtually the same time as the R-wave, and is thus hidden by this large electrical signal.

A normal heart rate varies between 60 to 100 beats per minute with an average of 72 bpm resulting in approximately 100,000 heartbeats per day. The heartbeat normally increases during periods of stress (physical or emotional) and slows during periods of rest (sleep).

The amount of blood that the heart pumps in one minute is called the cardiac output. It is calculated by the amount of blood ejected with each heartbeat (stroke volume) multiplied by the number of heart beats in a minute. If the heart rate is too slow to meet the physiologic requirements of the body, the cardiac output will not be sufficient to meet the metabolic demands of the body. Too slow of a heart rate, termed a bradycardia, may thus result in one of two major symptoms: (1) if the heart effectively stops with no heartbeat, there will be no blood flow and if this is sustained for a critical period of time (10 to 30 seconds), the individual will faint; or (2) if there is a heartbeat but it is too slow, the patient will be tired and weak (termed low cardiac output).

A pacemaker is a medical device that is used to selectively stimulate the heart with electrical stimulation pulses aimed at assisting it to perform its function as a pump. Normally, the stimulation pulses are timed to keep the heart rate above a prescribed limit, i.e., to treat a bradycardia. A pacemaker may thus be considered as a pacing system. The pacing system is comprised of two major components. One component is a pulse generator which generates the stimulation pulse and includes the electronic circuitry and the power cell or battery. The other is the lead or leads which electrically couple the pacemaker to the heart.

The pacemaker delivers an electrical stimulus to the heart to cause the heart to contract when the patient's own intrinsic rhythm fails. To this end, pacemakers include sensing circuits that sense the EGM, and in particular that sense the P-waves and/or R-waves in the EGM. By monitoring such P-waves and/or R-waves, the pacemaker circuits are able to determine the intrinsic rhythm of the heart, and provide stimulation pulses that force atrial and/or ventricular depolarizations at appropriate times in the cardiac cycle so as to help stabilize the electrical rhythm of the heart.

Pacemakers are described as either single-chamber or dual-chamber systems. A single-chamber system stimulates and senses the same chamber of the heart (atria or ventricle). A dual-chamber system stimulates and/or senses in both chambers of the heart (atria and ventricle). Dual-chamber systems may typically be programmed to operate in either a dual-chamber mode or a single-chamber mode.

A three letter code (sometimes expanded to a five letter code) is used to describe the basic mode in which the pacemaker is operating. These three letters refer specifically to electrical stimulation for the treatment of bradycardias. A fourth position (when used) identifies the degree of programmability and rate modulation, and a fifth position (when used) refers to electrical stimulation therapy for the primary treatment of fast heart rhythms or tachyarrhythmias or tachycardias.

The first position of the pacemaker code identifies the chamber to which the electrical stimulus is delivered. If the device is not capable of bradycardia support pacing, a "O" occupies this first position. If the unit paces in the ventricle, this is identified by a "V"; if it paces in the atrium, the first position is identified as an "A". If stimuli can be delivered to either the atrium or ventricle, the letter "D" is used to reflect dual-chamber stimulation.

The second position of the pacemaker code identifies the chamber or chambers in which sensing occurs. Sensing is the ability of the pacemaker to recognize the intrinsic electrical activity of the heart. The letters used in this position are identical to those used in the first position.

The third position of the pacemaker code identifies the way the pacemaker responds to a sensed signal. An "I" means that the pacemaker will be inhibited. When it senses or sees an intrinsic electrical signal, it inhibits its own output pulse and resets one or more internal timers within the pacemaker's circuitry. The other basic response is represented by a "T", which means triggered. The triggered mode of response indicates that when the pacemaker senses an intrinsic electrical signal, it not only resets various internal timers within the pacemaker, it also initiates or releases a stimulus in response to that sensed event. A "D" in the third position refers to both modes of sensing response. Most commonly, a sensed signal arising from the atrium and sensed on the atrial channel of a dual-chamber pacemaker will inhibit the atrial output but trigger a ventricular output after a brief delay (the AV delay). If a native ventricular depolarization does not occur before the AV delay timer completes, a ventricular stimulus will be released at the end of this AV delay. If a native ventricular signal is sensed within the AV delay, the ventricular output will be inhibited and other timers will be reset. If a native ventricular signal is sensed before the atrial stimulus is released, both the atrial and ventricular output pulses will be inhibited and the various timers will be reset.

A popular mode of operation for dual-chamber pacemakers is the DDD mode. DDD systems were developed to overcome the limitations of previous pacing methods. Specifically, DDD systems provide atrial pacing during atrial bradycardia, ventricular pacing during ventricular bradycardia, and atrial and ventricular pacing during combined atrial and ventricular bradycardia. In addition, DDD systems provide an atrial synchronous mode. Such features more closely approximate the normal response to exercise, or other physiological activity demanding a faster heart rate, by permitting a rate increase to occur commensurate with the rate of the sensed P-wave. This advantageously increases cardiac output and facilitates maintenance of AV synchrony.

Unfortunately, a pacemaker operating in the DDD mode may also cause a pacemaker mediated tachycardia (PMT). For example, in patients who are prone to atrial arrhythmias, e.g., a fast atrial rate, the DDD pacer tracks the fast atrial rate, causing the ventricles to be paced at a correspondingly fast rate, thereby causing a tachycardia (fast heart rate) to occur. Without the DDD pacemaker, such tachycardia would not occur in those patients with complete AV block because the ventricles would normally continue at a slower (more normal) rate, despite the fast atrial rate. However, with the DDD pacemaker, the stimulation of the ventricles occurs so as to track the fast atrial rate, and thus the pacemaker effectively intervenes or "mediates" so as to cause the tachycardia, appropriately termed a "pacemaker mediated tachycardia", or PMT, to occur.

An other reason why a PMT is triggered, other than simply tracking a fast atrial rate, is related to retrograde conduction of P-waves, which retrograde P-waves are sensed by the pacemaker atrial sensing circuit. A retrograde P-wave is caused by an R-wave conducting via a pathway to the atrium, thereby causing a retrograde P-wave. Unfortunately, the pacemaker atrial sensing circuit cannot differentiate between retrograde P-waves and normal P-waves, so such sensing throws off the pacemaker timing. Such disrupted timing may cause additional instabilities in the paced rhythm, which in turn may cause yet additional retrograde conduction, causing the process to repeat, leading eventually to a PMT. It is thus apparent that what is needed is a dual-chamber pacemaker that enhances its upper rate behavior so as to maintain a more constant ventricular rate, thereby minimizing the risk of a PMT.

Several approaches are known in the art to minimize the likelihood of a PMT in patients having a dual-chamber pacing system. For example, for patients who are particularly prone to atrial arrhythmias and where tracking of fast atrial rates is not desirable, the pacing system can simply be programmed to operate in a DDI mode. The DDI mode operates the same as the DDD mode except that the atrial signals (P-waves) are not tracked. Hence, detection of P-waves in the DDI mode results in inhibition of atrial output, with normal ventricular timing.

Unfortunately, even when pacing in the DDI mode, a retrograde P-wave may occur as a result of ventricular stimuli if the patient has retrograde conduction. Such retrograde P-wave, in turn, may result in low cardiac output, resulting in a condition which may be referred to as pacemaker mediated retrograde rhythm (PMRR). What is needed, therefore, is a way of detecting a PMRR when operating in the DDI mode of operation, and adjusting the DDI operation so as to terminate the PMRR.

SUMMARY OF THE INVENTION

The present invention addresses the above and other needs by providing a dual-chamber implantable pacemaker capable of operating in the DDI mode that detects when a pacemaker mediated retrograde rhythm (PMRR) occurs. Advantageously, in response to detecting a PMRR, the pacemaker of the present invention automatically alters the DDI operation so as to terminate the PMRR.

To operate in the DDI mode, the pacemaker of the present invention includes conventional sensing means for sensing the occurrence of atrial depolarizations (P-waves) and ventricular depolarizations (R-waves). Further, the pacemaker includes conventional pulse generating means for generating, at appropriate times within the cardiac cycle, an atrial stimulation pulse (A-pulse) and/or a ventricular stimulation pulse (V-pulse) in order to achieve the desired DDI operation. In accordance with the DDI mode, a given pacing cycle begins with a ventricular event, i.e., either the sensing of an R-wave or the generating of a V-pulse. An atrial escape interval (AEI) and a post ventricular atrial refractory period (PVARP) begin to time-out simultaneously as the DDI pacing cycle begins. Except as indicated below, no P-wave sensing occurs during the PVARP. Absent the sensing of a P-wave during the period after the PVARP and before the timing out of the AEI (which period of time may be considered as an alert zone or period), an A-pulse is generated when the AEI times out, and an A-V delay (AVD) commences. If a P-wave is sensed during the alert zone or period, then the generation of the A-pulse at the conclusion of the AEI is inhibited, but the AEI still must time-out before the AVD commences. The DDI pacing cycle continues until the next ventricular event, i.e., until either the sensing of an R-wave prior to the timing out of the AVD (in which case the DDI pacing cycle has a duration equal to the AEI plus an interval AR, where AR represents the time interval from the start of the AVD to the sensing of the R-wave), or the timing out of the AVD without having sensed an R-wave and the generation of a V-pulse (in which case the DDI pacing cycle has a duration equal to the AEI plus the AVD).

In accordance with one aspect of the invention, a P-wave that occurs during a relative refractory portion of the PVARP may be sensed, and is presumed to be a retrograde P-wave. When retrograde P-wave sensing is employed in this manner, a P-wave that occurs during the relative refractory portion of PVARP triggers the generation of an A-pulse a fixed time delay, e.g., 300 msec, thereafter. The generation of an A-pulse a fixed time delay after the presumed retrograde P-wave will normally prevent the occurrence of a PMRR.

In accordance with another aspect of the invention, a PMRR is detected by measuring the P-to-V time interval in any pacing cycle of the DDI operation that terminates in the generation of a ventricular stimulation pulse (V-pulse). In the absence of a PMRR, the P-to-V time interval should be relatively short, generally not much longer than the programmed AV delay (AVD) of the normal DDI pacing cycle. However, in the presence of a PMRR, a retrograde P-wave occurs relatively early in the DDI pacing cycle, so the P-to-V time interval will be significantly longer than without the PMRR. Hence, in accordance with the present invention, a PMRR is presumed to be present whenever the measured P-to-V interval exceeds a prescribed time interval, $T_B$. The interval $T_B$ may be a programmable value, e.g., approximately 300 msec.

In accordance with yet another aspect of the invention, a PMRR is presumed to be present only when a programmed number n of consecutive P-to-V time intervals, each greater than a prescribed time interval, occurs. For example, if n equals 10, then a PMRR is detected to be present only if ten consecutive P-to-V intervals occur, where each of the ten P-to-V time intervals is greater than the prescribed time interval, $T_B$.

In accordance with still another aspect of the invention, once a PMRR is detected, the pacemaker automatically alters its DDI operation so as to terminate the PMRR. In a preferred embodiment, this is done by extending the post-ventricular atrial refractory period (PVARP) by a sufficient amount so as to block the sensing of any retrograde P-waves that may be occurring. As soon as the extended PVARP terminates, an alert time interval, $T_{ALERT}$, begins and continues until the end of the AEI. This allows the duration of the $T_{ALERT}$ interval (which is equal to the difference between the AEI and the extended PVARP) to be of sufficient length to allow atrial tissue to repolarize and/or to detect a normal P-wave. Should a P-wave be sensed during the $T_{ALERT}$ interval, then the generation of an A-pulse at the conclusion of the AEI is inhibited. Should no P-wave be sensed during the $T_{ALERT}$ interval, which will normally be the case for a PMRR, then an A-pulse is generated at the conclusion of the AEI. Advantageously, such A-pulse prevents the next ventricular event from triggering a retrograde P-wave, thereby terminating the PMRR.

In accordance with an additional aspect of the invention, if no P-waves are sensed during the alert period, causing the pacemaker to pace in the atrium, the AEI is extended, when necessary, to assure a minimum time interval between the last sensing of a P-wave and such pacing in the atrium, i.e., the next A-pulse. Such AEI extension, which is particularly suitable for rate-responsive pacing when the AEI could otherwise be set to be quite short, assures such A-pulse will not be delivered to the atria while they are still refractory following the P-wave, thereby helping to assure the A-pulse is able to capture the atria.

It is thus a feature of the invention to provide an implantable pacemaker that, when operating in a DDI mode, is able to detect a PMRR and automatically respond to such PMRR by modifying the DDI operation so as to terminate the PMRR.

It is another feature of the invention to provide an implantable DDI pacemaker that extends the post-ventricular atrial refractory period upon detection of a PMRR, thereby preventing detection of any retrograde P-waves that may occur in the next pacing cycle, and then pacing in the atrium, thereby preventing the next ventricular event from causing a retrograde P-wave, and thereby terminating the PMRR.

It is yet an additional feature of the invention, in accordance with one embodiment thereof, to sense P-waves that occur during the relative refractory portion of the PVARP and to presume that such sensed P-waves are retrograde P-waves, and to generate an A-pulse a prescribed time delay thereafter, thereby preventing such retrograde P-waves from establishing and maintaining a PMRR.

BRIEF DESCRIPTION OF THE DRAWINGS

The above and other aspects, features and advantages of the present invention will be more apparent from the following more particular description thereof, presented in conjunction with the following drawings wherein:

FIGS. 9-1 and 9-2 show a flow chart that illustrates the operation of a pacemaker made in accordance with the present invention in detecting and terminating a PMRR;

FIG. 10 shows a composite timing waveform diagram that illustrates a variation of the invention wherein P-waves are sensed during a latter portion of the PVARP interval and are presumed to be retrograde P-waves, with an A-pulse being generated a fixed delay thereafter;

FIG. 11 is an assembly block diagram that depicts the various electrical/electronic hardware assemblies and sub-assemblies of an implantable pacemaker made in accordance with a microprocessor-based embodiment of the invention;

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

In order to better understand the present invention, reference will first be made to FIG. 1, where there is shown a typical ECG-type waveform illustrating a normal cardiac cycle of a heart. Such waveforms may be obtained using conventional skin-electrode ECG techniques. Alternatively, intracardiac ECG features of modern pacemakers provide similar ECG information through the use of the telemetry features of such pacemakers.

Figure 1:
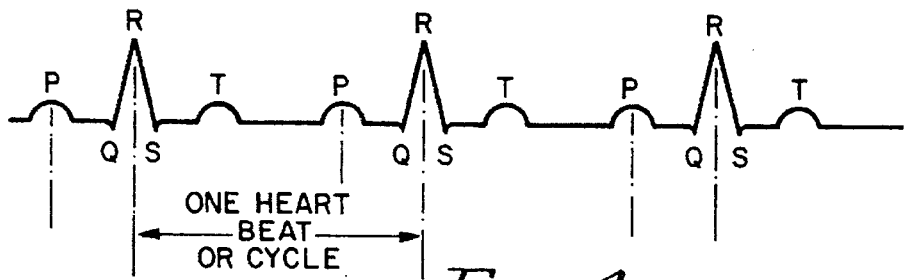
FIG. 1 is a typical-ECG-type waveform illustrating the normal AV synchrony of the heart.

Beginning at the left of the waveform of FIG. 1, there is shown a P-wave. This P-wave represents the electrical activity coincident with the depolarization of the atria of the heart, and the P-wave may thus be considered as an atrial depolarization signal. Depolarization of the atria is accompanied by the physical contraction of the atria, thereby allowing blood to be pushed from the atria into the ventricles of the heart.

A short time subsequent to the generation of the P-wave, the QRS complex appears, representing the depolarization of the ventricles. The QRS complex is often referred to simply as an R-wave, and such R-wave may thus be considered as a ventricular depolarization signal. Depolarization of the ventricles is accompanied by the physical contraction of the ventricles, thereby allowing blood to be pushed from the ventricles into the circulatory system of the patient's body. The time period between the P-wave and the R-wave is an important time interval in the operation of the heart because it represents the time needed for the blood to flow from the atria into the ventricles. The R-wave is followed by a T-wave, which wave represents the electrical activity associated with the repolarization of the ventricles.

As known to those skilled in the art, the ventricles do most of the work in pumping the blood throughout the body. Typically, one heartbeat or heart cycle is measured as the time interval between successive R-waves, simply because the R-wave represents the easiest of the waves to identify and measure. A heartbeat may, of course, be measured relative to any point within the heart cycle, such as between succeeding T-waves or P-waves.

A certain rhythm or synchrony must occur if the heart is to perform its function of a pump efficiently. That is, the depolarization of the atria, represented by the P-wave, must be followed a short time thereafter by the depolarization of the ventricles, represented by the R-wave. After a sufficient delay, the atria must again depolarize, followed by the depolarization of the ventricles. If the depolarization of the atria or ventricles do not occur naturally, then a pacemaker may be employed to provide stimulation pulses to these respective heart chambers in order to trigger the required depolarization/contraction at the appropriate time periods of the heart cycle. Note that the "heart cycle", e.g., the time period between successive ventricular depolarizations, may also be referred to herein as a "pacing cycle", particularly when a pacemaker provides stimulation pulses in order to maintain such cycle.

When a stimulation pulse is provided to the atrium by a pacemaker, such pulse is referred to herein as an atrial stimulation pulse, or simply an "A-pulse". When a stimulation pulse is provided to the ventricles, such pulse is referred to herein as a ventricular stimulation pulse, or simply a "V-pulse". It is thus the basic function of a pacemaker to monitor the depolarization signals (R-waves and/or P-waves) generated by the heart and provide stimulation pulses when needed within the pacing cycle in order to maintain a desired heart rhythm.

Figure 2:
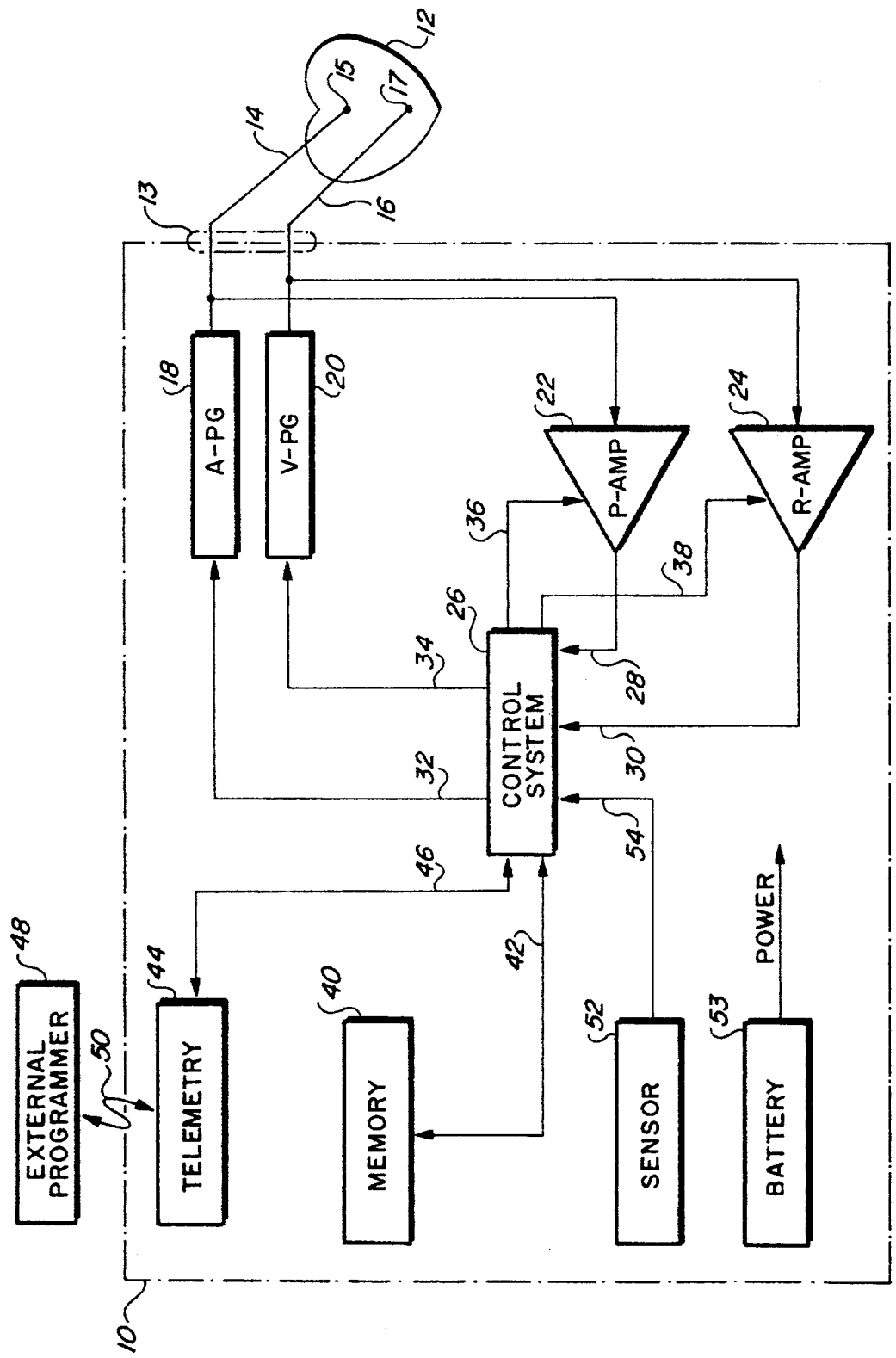
FIG. 2 shows a block diagram of an implantable, programmable, dual-chamber pacemaker coupled to an external programmer.

Referring next to FIG. 2, a simplified block diagram of a dual-chamber pacemaker 10 is illustrated. The pacemaker 10 is coupled to a heart 12 by way of leads 14 and 16, the lead 14 having an electrode 15 that is in contact with one of the atria of the heart, and the lead 16 having an electrode 17 that is in contact with one of the ventricles of the heart. The leads 14 and 16 are electrically and physically connected to the pacemaker 10 through a connector 13 that forms an integral part of the housing wherein the circuits of the pacemaker are housed. The leads 14 and 16 carry stimulating pulses to the electrodes 15 and 17 from an atrial pulse generator (A-PG) 18 and a ventricular pulse generator (V-PG) 20, respectively. Further, electrical signals from the atria are carried from the electrode 15, through the lead 14, to the input terminal of an atrial channel sense amplifier (P-AMP) 22; and electrical signals from the ventricles are carried from the electrode 17, through the lead 16, to the input terminal of a ventricular channel sense amplifier (R-AMP) 24.

Controlling the dual-chamber pacer 10 is a control system 26. (Note that throughout this application, the terms "pacemaker" and "pacer" may be used interchangeably.) The control system 26 receives the output signals from the atrial (P-AMP) amplifier 22 over signal line 28. Similarly, the control system 26 receives the output signals from the ventricular (R-AMP) amplifier 24 over signal line 30. These output signals are generated each time that a P-wave or an R-wave is sensed within the heart 12. The control system 26 also generates trigger signals that are sent to the atrial pulse generator (A-PG) 18 and the ventricular pulse generator (V-PG) 20 over signal lines 32 and 34, respectively. These trigger signals are generated each time that a stimulation pulse is to be generated by the respective pulse generator 18 or 20. The atrial trigger signal is referred to simply as the "A-trigger", and the ventricular trigger signal is referred to as the "V-trigger". During the time that either an A-pulse or V-pulse is being delivered to the heart, the corresponding amplifier, P-AMP 22 and/or R-AMP 24, is typically disabled by way of a blanking signal presented to these amplifiers from the control system over signal lines 36 and 38, respectively. This blanking action prevents the amplifiers 22 and 24 from becoming saturated from the relatively large stimulation pulses that are present at their input terminals during this time. This blanking action also helps prevent residual electrical signals present in the muscle tissue as a result of the pacer stimulation from being interpreted as P-waves or R-waves.

Still referring to FIG. 2, the pacer 10 also includes a memory circuit 40 that is coupled to the control system 26 over a suitable data/address bus 42. This memory circuit allows certain control parameters, used by the control system 26 in controlling the operation of the pacemaker, to be programmably stored and modified, as required, in order to customize the pacer's operation to suit the needs of a particular patient. Further, data sensed during the operation of the pacer may be stored in the memory 40 for later retrieval and analysis.

A telemetry circuit 44 is further included in the pacer 10. This telemetry circuit 44 is connected to the control system 26 by way of a suitable command/data bus 46. In turn, the telemetry circuit 44, which is included within the implantable pacer 10, may be selectively coupled to an external programming device 48 by means of an appropriate communication link 50, which communication link 50 may be any suitable electromagnetic link, such as an RF (radio frequency) channel, a magnetic link, an inductive link, an optical link, and the like. Advantageously, through the external programmer 48 and the communication link 50, desired commands may be sent to the control system 26. Similarly, through this communication link 50 and the programmer 48, data (either held within the control system 26, as in a data latch, or stored within the memory 40) may be remotely received from the pacer 10. In this manner, noninvasive communications can be established with the implanted pacer 10 from a remote, non-implanted, location.

The pacer 10 additionally includes a battery 53 which provides operating power to all of the circuits of the pacer 10 via the POWER signal line.

The pacer 10 in FIG. 2 is referred to as a dual-chamber pacemaker because it interfaces with both the atria and the ventricles of the heart. Those portions of the pacer 10 that interface with the atria, e.g., the lead 14, the P-wave sense amplifier 22, the A-pulse generator 18, and corresponding portions of the control system 26, are commonly referred to as the "atrial channel". Similarly, those portions of the pacer 10 that interface with the ventricles, e.g., the lead 16, the R-wave sense amplifier 24, the V-pulse generator 20, and corresponding portions of the control system 26, are commonly referred to as the "ventricular channel".

In accordance with one embodiment of the present invention, the pacemaker 52 further includes a sensor 52 that is connected to the control system 26 of the pacer over a suitable connection line 54. While this sensor 52 is illustrated in FIG. 1 as being included within the pacer 10, it is to be understood that the sensor may also be external to the pacer 10, yet still be implanted within or carried by the patient. A common type of sensor is an activity sensor, such as a piezoelectric crystal, that is mounted to the case of the pacemaker. Other types of sensors are also known, such as sensors that sense the oxygen content of blood, respiration rate, pH of blood, body motion, and the like. The type of sensor used is not critical to the present invention. Any sensor that is capable of sensing some parameter that is relatable to the rate at which the heart should be beating can be used. Such sensors are commonly used with "rate-responsive" pacemakers in order to adjust the rate (pacing cycle) of the pacer in a manner that tracks the physiological needs of the patient.

It is noted that the telemetry circuit 44 may be of conventional design, such as is described in U.S. Pat. No. 4,944,299, or as is otherwise known in the art. Similarly, the external programmer 48 may be of any suitable design known in the art, such as is described in U.S. Pat. No. 4,809,697. The '299 and '697 patents are incorporated herein by reference. Likewise, the memory circuit 40, and the circuits utilized in the atrial and ventricular channels may all be of common design as is known in the pacing art. The present invention is not concerned so much with the details of the circuitry utilized for each of these pacing elements, as it is with the manner in which all of these pacing elements cooperate with each other in order to provide a particular pacing mode of operation. Such cooperation is controlled by the control system 26. Hence, a more detailed description of the control system 26 is presented below.

Figure 6:
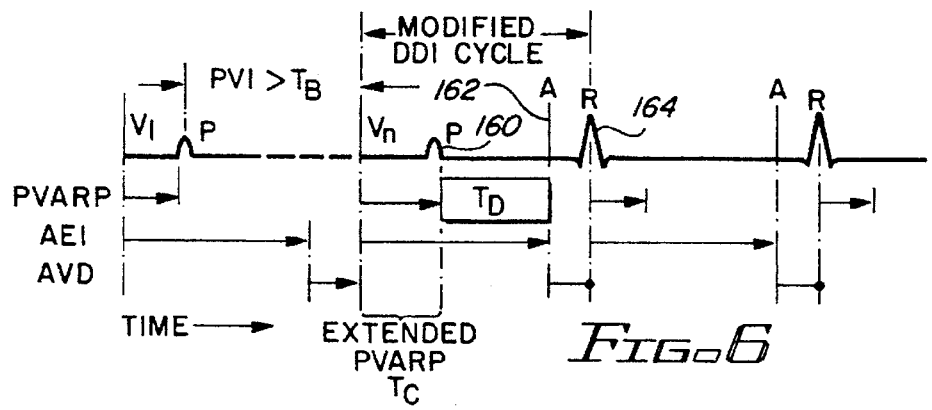
FIGS. 6 and 7 likewise show composite timing waveform diagrams and illustrate how the DDI operation of the pacemaker is altered in order to terminate the PMRR.
Figure 7:
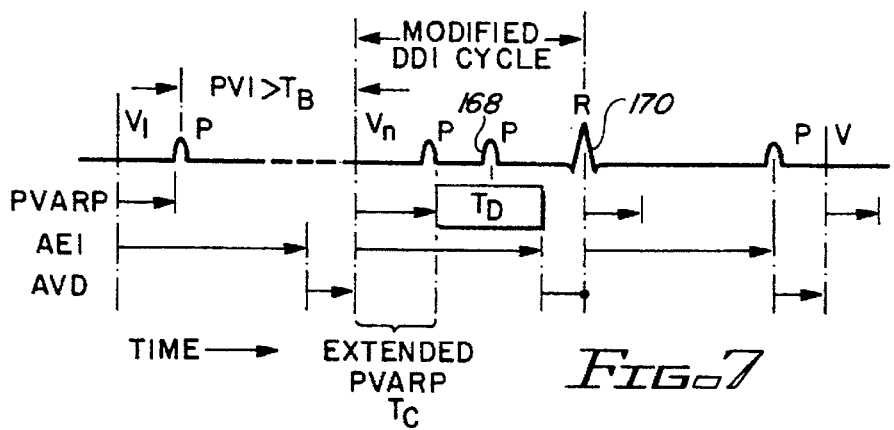
Figure 8:
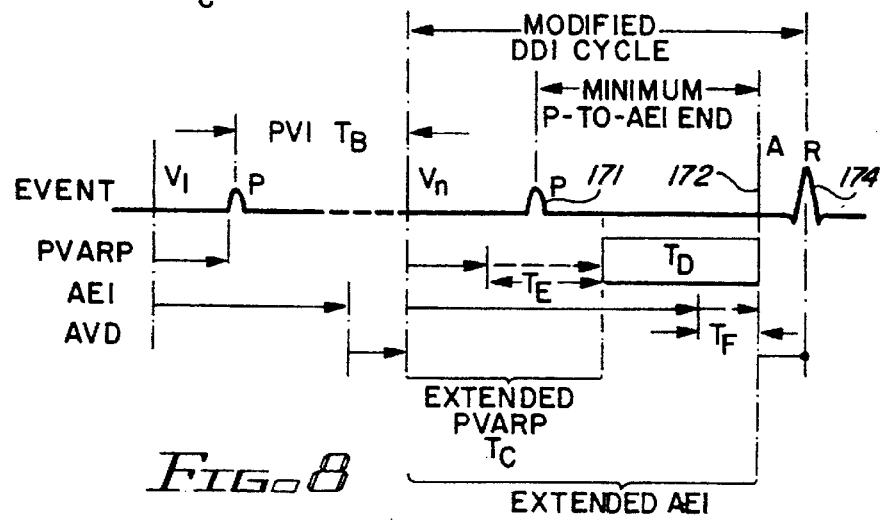
FIG. 8 is a composite timing waveform diagram, similar to FIGS. 6 and 7, that illustrates how the AEI may be extended by the DDI or DDIR operation in order to assure that there is at least a prescribed time interval, e.g., 300 msec, between a sensed P-wave and the next A-pulse.

It is noted that in accordance with the present invention the control system 26 may be realized using a variety of different techniques and/or circuits. For example, the control system 26 may be a microprocessor-based control system, as described below in conjunction with FIGS. 11–14. Still further, the control system 26 may be realized using a state machine as described below in conjunction with FIG. 3. Indeed, any type of control circuit or system could be employed. The present invention is not concerned so much with the details of the control system 26, as it is with the end result achieved by the control system. That is, so long as the control system 26 controls the operation of the pacemaker so that the desired timing relationships set forth below in FIGS. 6, 7, and 8 are achieved, e.g., by following the steps described below in the flow chart of FIGS. 9-1 and 9-2, it does not matter what type of control system is used. Those of skill in the pacemaker art, given the teachings presented herein, should thus be able to fashion numerous different types of control systems or circuits that achieve the desired pacemaker control.

A detailed description of the types of control circuits that may be used for the control system 26 of FIG. 2, or the circuits which make up the control system 26, will not be presented at this point of the description. Such circuits may be conventional, or may be patterned after known circuits available in the art. Reference is made, for example, to the microprocessor-based control system described in U.S. Pat. No. 4,940,052, entitled "Microprocessor Controlled Rate-Responsive Pacemaker Having Automatic Rate Response Threshold Adjustment". Reference is also made, for example, to U.S. Pat. Nos. 4,712,555 and 4,944,298, wherein a state-machine type of operation for a pacemaker is described; and U.S. Pat. No. 4,788,980, wherein the various timing intervals used within the pacemaker and their inter-relationship are more thoroughly described. The '052, '555, '298 and '980 patents are incorporated herein by reference.

Figure 3:
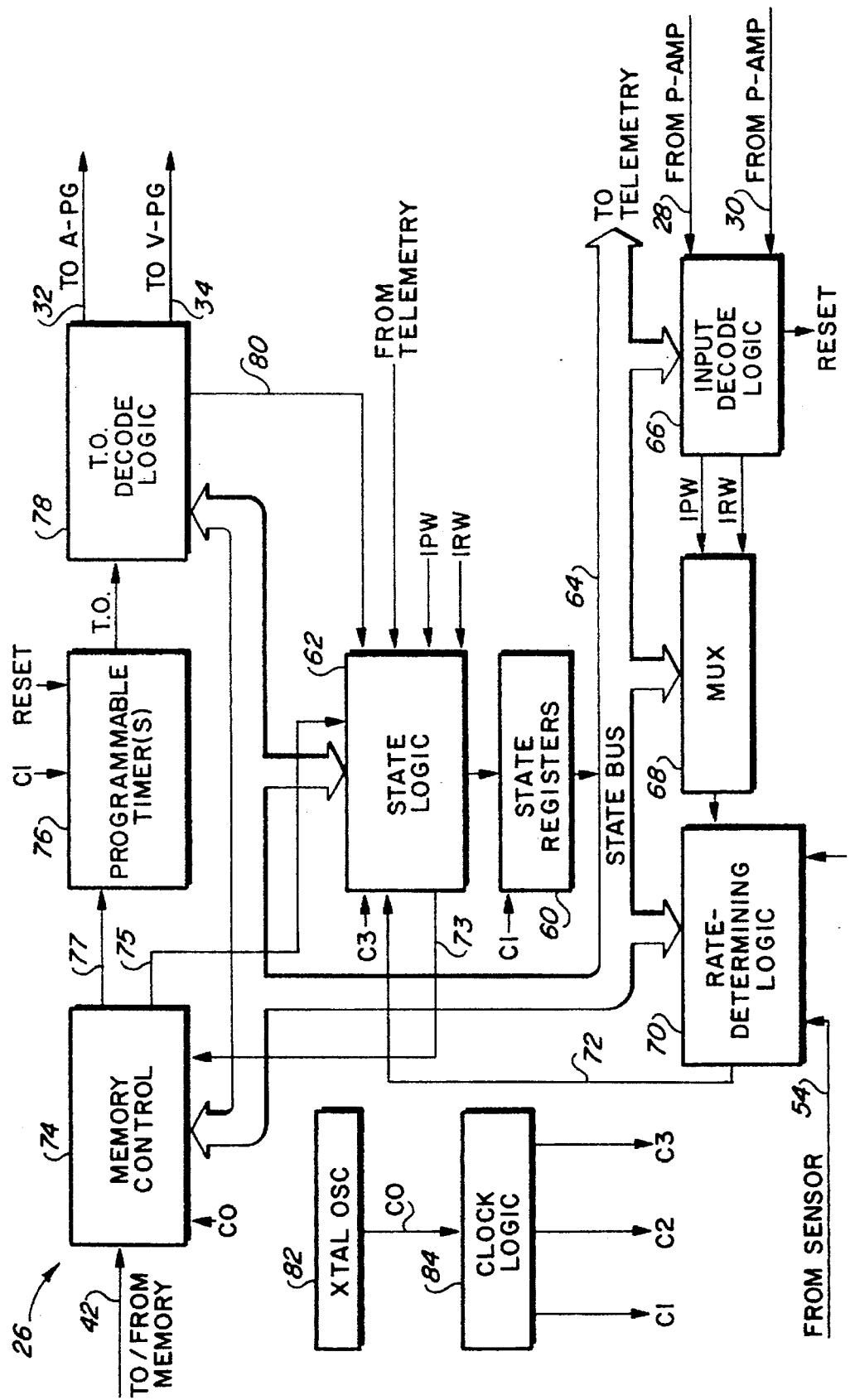
FIG. 3 is a block diagram of one possible embodiment of the control system of the pacemaker of FIG. 2.

Additional details regarding a preferred control system 26 for a pacer operating in accordance with the present invention are presented below in the section entitled "Microprocessor-Based Pacemaker," where a more detailed description of FIGS. 11–14 is presented. Additional details regarding an alternate control system 26 are also presented below in the section entitled "State-Machine-Based Pacemaker," where a more detailed description of FIG. 3 is presented.

Because various types of control systems 26 may be used with the invention, it is convenient to describe the present invention in terms of the various timing intervals that time-out or are reset during the sequence of events that make up a pacing cycle. (In some instances, several time intervals may time-out in parallel, while in other instances, the timing intervals may occur sequentially, one following the other. The implementation, including the starting, resetting, and timing out, of such timing intervals is controlled by the control system 26 in conventional manner.) Hence, in the description that follows, reference is made to such timing intervals. Those of skill in the art will be able to design an appropriate pacemaker control system that provides pacing cycles made up of the timing intervals described. Further, such pacing intervals are not dependent upon the type of control system that is used. Thus, the present invention may be practiced regardless of whether the pacemaker is based on a microprocessor-based system, as described below in connection with FIGS. 11–14 (or in some of the referenced patents); a state machine, as described below in connection with FIG. 3; or whether based on other circuit designs that perform the same or similar functions.

In describing the timing intervals that are generated by the control system 26 in order to carry out the invention, only the main or basic timing intervals that make up the pacing cycle are described. Some common and always-present intervals, such as the blanking intervals that exist after a stimulation pulse is generated, are assumed to be present, but are not shown or described.

Figure 4:
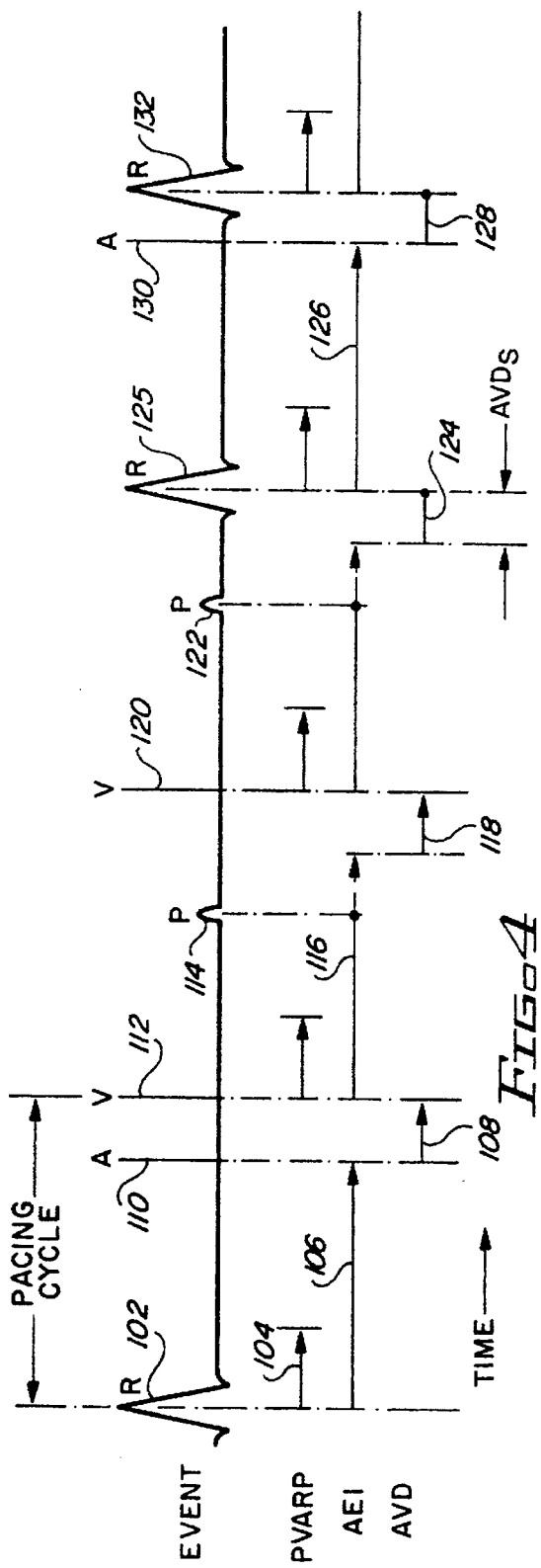
FIG. 4 is a composite timing waveform diagram that illustrates cardiac depolarization and stimulation signals as a function of selected timing intervals generated within the pacemaker of FIG. 2 when operating in a DDI mode of operation.

Referring then to FIG. 4, there is shown a composite timing waveform diagram that illustrates cardiac depolarization and stimulation signals as a function of selected timing intervals generated within the pacemaker of FIG. 2 when operating in a DDI mode of operation. It is noted that in the composite timing waveform diagram of FIG. 4, as well as the other composite timing waveform diagrams presented herein, time is indicated along the horizontal axis, with an increase or passage of time occurring as one moves from left to right in the figure. Several events are shown as separate channels along the vertical axis, including a symbolic representation of certain cardiac events (EVENTS), a post-ventricular atrial refractory period (PVARP), an atrial escape interval (AEI), and an A-V delay (AVD). The cardiac events of concern for purposes of the present invention include an R-wave, a P-wave, an A-pulse and a V-pulse, and hence those are the only events shown.

During conventional DDI pacing, as is shown in FIG. 4, a pacing cycle begins with the occurrence of a ventricular event, e.g., an R-wave 102. The occurrence of the R-wave 102 triggers the start of a PVARP, represented by the horizontal line 104, and the start of an AEI, represented by the horizontal line 106. In the DDI mode, the AEI is always allowed to time-out, regardless of whether a P-wave is sensed as it times out. The AEI is followed by the AVD, represented in FIG. 4 by the line 108 (and hereafter referred to as simply the AVD 108). Typically, the PVARP is of a programmed duration, e.g., 100–300 msec. The AEI is usually used, in conjunction with the AVD, to define the pacing period or "pacing cycle". Thus, the AEI is computed to be of whatever duration is needed to provide the basic programmed pacing rate of the pacemaker. Alternatively, for rate-responsive pacing, the AEI is computed to be a function of the sensor indicated rate. The AVD is also usually a fixed (programmed) duration, although some pacemaker models allow the AVD to adaptively change depending upon whether a P-wave or A-pulse precedes the AVD, and/or as a function of the sensor indicated rate (if rate-responsive pacing is employed).

The AEI is usually of much longer duration than the PVARP. Hence, the PVARP times out first. In FIG. 4, and the other composite timing waveform diagrams presented herein, when a given time interval times out, such timing out is indicated by placing an arrow head at the right end of the line that represents the timing interval. Similarly, if some event occurs before the timing out of the time interval, the occurrence of such event is represented by placing a dot along the line representing the time interval.

The purpose of the PVARP is to prevent sensing of P-waves (or other artifacts in the ECG-type waveform being monitored by the pacemaker that may be interpreted by the pacemaker as P-waves) during that period after a ventricular event (i.e., "post-ventricular") during which the atrium is still refractory or repolarizing.

During the first pacing cycle shown in FIG. 4, no cardiac events occur during the timing out of the AEI 106. Hence, upon the timing out of the AEI 106, an A-pulse 110 is generated, and the AVD 108 commences. During the timing out of the AVD 108, no further cardiac events are sensed. Thus, upon the timing out of the AVD 108, a V-pulse 112 is generated.

The generation of the V-pulse 112 signifies the end of the first pacing cycle and the commencement of the next pacing cycle. Hence, another AEI 116 commences after the V-pulse 112 is generated. During the next pacing cycle, i.e., during the timing out of the AEI 116, a P-wave 114 occurs. For DDI pacing, such occurrence does not reset the AEI, but serves only to inhibit the generation of an A-pulse at the end of the AEI 116. Thus, upon the timing out of the AEI 116, no A-pulse is generated, but the timing out of the AEI 116 does trigger the commencement of the next AVD 118.

As shown in FIG. 4, no R-wave is sensed during the timing out of the AVD 118. Hence, upon the timing out of the AVD 118, a V-pulse 120 is generated. The generation of the V-pulse 120 signifies the ventricular event that starts the next pacing cycle. During this next pacing cycle, another P-wave 122 is sensed. Hence, at the conclusion of the AEI corresponding to this pacing cycle, the generation of an A-pulse is inhibited, and a new AVD 124 commences. Before the AVD 124 times out, an R-wave 125 occurs. Such occurrence immediately terminates (resets) the AVD 124 and starts the next cardiac cycle. The next cardiac cycle includes an AEI 126, followed by an AVD 128. No P-wave is sensed during the timing out of the AEI 126, so an A-pulse 130 is generated at the conclusion thereof. However, an R-wave 132 is sensed during the timing out of the AVD 128, causing the AVD to be reset and immediately terminating the pacing cycle.

Thus, as seen in FIG. 4, four possible types of pacing cycles are illustrated for DDI operation. The first pacing cycle type includes the A-pulse 110 and terminates with the V-pulse 112; the second includes the P-wave 114 and terminates with the V-pulse 120; the third includes the P-wave 122 and terminates with the R-wave 125; and the fourth includes the A-pulse 130 and the R-wave 132. Each pacing cycle is made up of two main timing components: the AEI and the AVD. If no R-waves are sensed, the AVD is allowed to time-out, a V-pulse is generated, and the pacing cycle has a duration of AEI+AVD. If an R-wave is sensed, the AVD is cut short, e.g., to a value $AVD_S$, and the pacing cycle has a duration of $AEI+AVD_S$. An A-pulse is generated only at the conclusion of the AEI if no P-wave is sensed during the time interval between the end of the PVARP and the timing out of the AEI.

Figure 5:
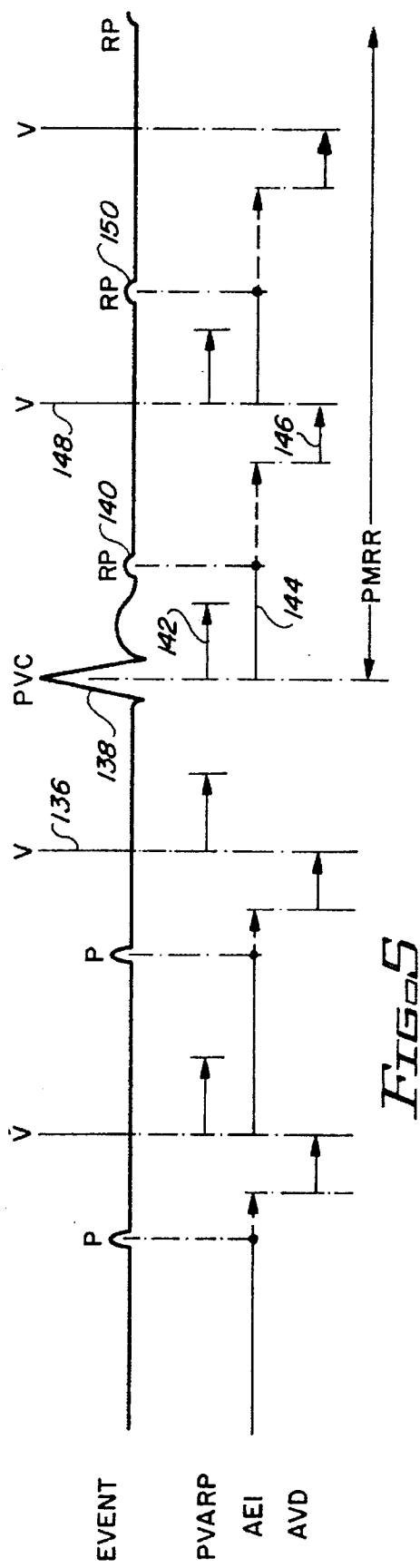
FIG. 5 is a composite timing waveform diagram as in FIG. 4 that illustrates a pacemaker mediated retrograde rhythm (PMRR)

Turning next to FIG. 5, a composite timing waveform diagram is shown as in FIG. 4 that illustrates a pacemaker mediated retrograde rhythm (PMRR). As seen in FIG. 5, the left portion of the composite timing waveform diagram illustrates conventional DDI pacing, as in FIG. 4. That is, prior to the PMRR, the pacing cycles have a duration of AEI+AVD, as described above. However, as seen in FIG. 5, a premature ventricular contraction (PVC) 138 occurs during the pacing cycle that commences with the V-pulse 136. The PVC 138 is treated by the pacing circuits as a ventricular event, thus starting a new pacing cycle, including a new PVARP 142 and a new AEI 144. In some instances, and as shown in FIG. 5, such PVC 138 may cause a retrograde P-wave (RP) 140 to occur. The RP 140 is sensed by the atrial channel of the pacemaker because it occurs after the termination of the PVARP 142. Hence, at the conclusion of the AEI 144, A-pulse generation is inhibited, and a new AVD 146 begins. The AVD 146 terminates without the sensing of an R-wave, thus triggering the generation of a V-pulse 148. The V-pulse 148, like the PVC 138, causes another retrograde P-wave 150 to occur. This retrograde P-wave 150 inhibits the generation of an A-pulse at the termination of the current AEI, and the process repeats.

The repeated occurrence of a sequence of pacing cycles made up of a V-pulse, followed by a retrograde P-wave, is termed for purposes of the present invention a "pacemaker mediated retrograde rhythm" (PMRR). A PMRR is undesirable because the retrograde P-wave occurs too early in the pacing cycle to be of much hemodynamic benefit as the heart attempts to efficiently perform its function of a pump. That is, even though the basic ventricular pacing rate associated with a PMRR is not changed from that of a conventional DDI pacing cycle (the basic pacing cycle remains as AEI+ AVD), the relative timing between depolarization of the atrium and depolarization of the ventricles is incorrect, and the needed AV synchrony for maximizing cardiac output is absent.

In order to address the problem of a PMRR as shown in FIG. 5, a pacemaker 10 that operates in accordance with the present invention automatically: (1) detects the presence of a PMRR, and (2) alters or adjusts the operation of the next DDI pacing cycle after the PMRR detection so as to terminate the PMRR. The manner in which this is done is illustrated in the composite timing waveform diagrams of FIGS. 6 and 7. Further, in order to assure that an A-pulse generated by the pacemaker captures the atrium, and that the atrium will therefore be refractory to any retrograde P-waves that might occur, the invention also assures that at least a prescribed time period, e.g., 300 msec, must lapse between a sensed P-wave and the next A-pulse. This is done, as illustrated in FIG. 8, by extending the AEI as necessary to assure that the prescribed time period exists between the sensed P-wave and the next A-pulse.

To determine if a PMRR is present, the invention measures the P-to-V interval (PVI) in the DDI pacing cycle. In the absence of a PMRR, the normal AV synchrony of the heart maintains the PVI at a relatively small value compared to the duration of the pacing cycle. However, in the presence of a PMRR, the PVI extends to unusually long intervals. Thus, in accordance with the present invention, if the measured PVI is greater than a prescribed interval reference, $T_B$, then the pacemaker logic circuit assumes that a PMRR is present. The reference interval $T_B$ may be on the order of 250 to 350 msec, typically about 300 msec.

In measuring the PVI to determine if a PMRR is present, several different approaches may be taken. The PVI of a single pacing cycle may be measured and compared to the reference value $T_B$. Alternatively, the PVI of n consecutive pacing cycles may be measured and averaged, with the average PVI then being compared to the reference interval $T_B$. Still further, the PVI of n consecutive pacing cycles may be measured, with each measured value being compared to the reference interval $T_B$. Only if all of the PVI's of the n pacing cycles are greater than $T_B$ is a determination made that a PMRR is present. The value of n is a programmable integer, e.g., 1 to 32.

In FIG. 6, a composite timing waveform diagram is illustrated wherein n pacing cycles are presumed present, each starting with a V-pulse, from $V_1$ to $V_n$, and each having a PVI greater than $T_B$. The number n may be a programmable number, and will usually be a number ranging from 1 to 32, e.g., 10. Thus, after the nth pacing cycle having a PVI greater than $T_B$, a PMRR is presumed to be present. Once it has been determined that a PMRR is present, the invention extends the duration of the PVARP from its normal value (which usually ranges from 100 to 300 msec) to an extended value. Such extended PVARP is illustrated in FIG. 6 as being of a duration $T_C$. The value of $T_C$ may also be a programmable value, but will usually be on the order of about 500 msec, and should be selected to be sufficiently long to prevent retrograde P-waves from being sensed. Thus, as seen in FIG. 6, once the PVARP is extended to $T_C$, the next retrograde P-wave 160 is not sensed.

Following the extension of the PVARP, an alert period, $T_D$, is started during which the atrial channel is monitored to determine if a P-wave is sensed. The alert period $T_D$ lasts until the AEI times out. Thus, $T_D$ has a duration equal to the length of AEI minus $T_C$. If a P-wave is not sensed during the alert period $T_D$, as shown in FIG. 6, then an A-pulse 162 is generated at the conclusion (or timing out) of the AEI. Such A-pulse advantageously prevents the next ventricular event, which for the situation shown in FIG. 6 is an R-wave 164, from causing another retrograde P-wave. That is, by modifying the DDI pacing cycle as shown in FIG. 6, including pacing in the atrium with the A-pulse 162, and by extending the AEI as necessary in order to assure that there is at least a prescribed time interval between a sensed P-wave and the next A-pulse, as described below in conjunction with FIG. 8, the PMRR is effectively broken.

The composite waveform diagram of FIG. 7 is the same as is shown in FIG. 6 except that a P-wave 168 is sensed during the alert period $T_D$. However, such P-wave 168 occurs close-enough in time to the next ventricular event, the R-wave 170, to prevent such R-wave 170 from causing another retrograde P-wave. Hence, stimulation of the atrium with an A-pulse at the conclusion of the AEI is not needed, and is not provided, as the atrium would still be refractory.

It is noted that the present invention may be used with any pacemaker operating in a DDI mode or a DDIR mode. In a DDIR mode, or a rate-responsive DDI mode, the AEI and (in some pacemakers) the AVD are adjusted as a function of a sensed parameter, indicative of the physiological needs of the patient. In such a rate-responsive mode, the AEI (and possibly the AVD) may be adjusted to be extremely short. In such instances, the present invention is only effective if the A-pulse captures the atria to make them refractory to any retrograde P-waves that might otherwise occur. To assure the delivered A-pulse does capture the atria, it is important that there be a prescribed time period, e.g., 300 msec, between the sensing of a P-wave and the next atrial pulse, thereby assuring that the A-pulse is not delivered to the atria when they are refractory following the sensed P-wave. To ensure that such prescribed time period exists between a sensed P-wave and the delivery of an A-pulse, the present invention extends the AEI as required in order to force such prescribed time period to exist. Such AEI extension is illustrated in the composite waveform diagram of FIG. 8.

As seen in FIG. 8, n pacing cycles are presumed present, each starting with a V-pulse, from $V_1$ to $V_n$, and each having a PVI greater than $T_B$. After the $n^{th}$ pacing cycle having a PVI greater than $T_B$, a PMRR is presumed to be present, thus causing the duration of the PVARP to be extended by an amount $T_E$ from its normal value to a value $T_C$. The occurrence of any P-wave, such as the retrograde P-wave 171, that occurs during the extended portion of the PVARP, i.e., during the time interval $T_E$, is (like any P-wave that occurs during the PVARP) blocked from altering the pacemaker timing circuits for most purposes. However, the relative time of occurrence of the P-wave 171 within the cardiac pacing cycle is noted so that a determination can be made as to how much time remains from the sensing of the P-wave 171 to the end of the current AEI period. If such time is less than a prescribed time period, e.g., a minimum P-wave-to-AEI$_{END}$ time interval, then the AEI is extended by an amount, $T_F$, as shown in FIG. 8, in order to make up the difference. Thus, as evident from FIG. 8, the AEI+$T_F$ is equal to the time period up to the occurrence of the P-wave 171 plus the prescribed time period (the minimum P-wave-to-AEI$_{END}$ time interval). The next A-pulse 172 is generated at the conclusion of the extended AEI. The alert period $T_D$ remains in effect until the end of the extended AEI.

Figures 1, 9:
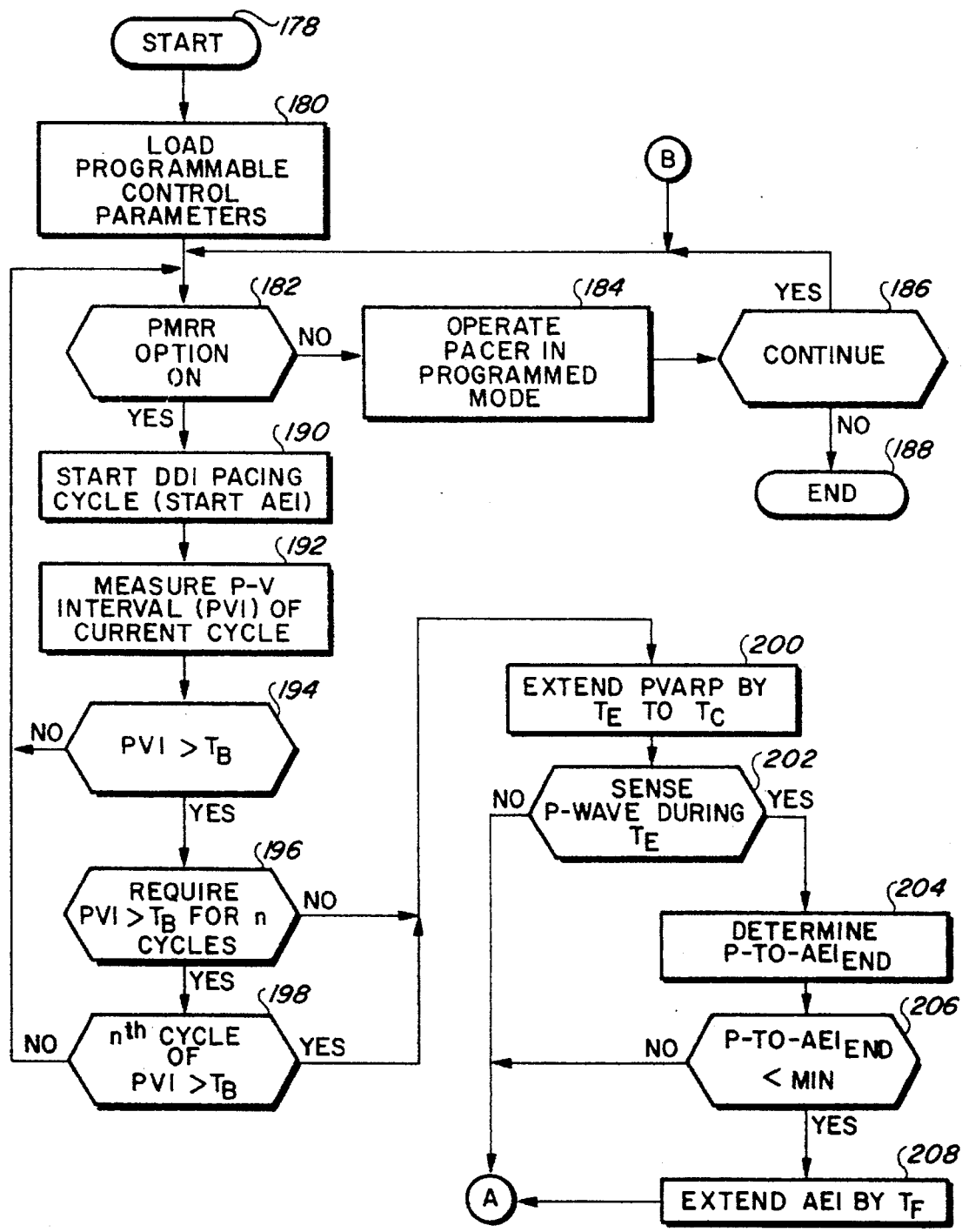
Figures 2, 9:
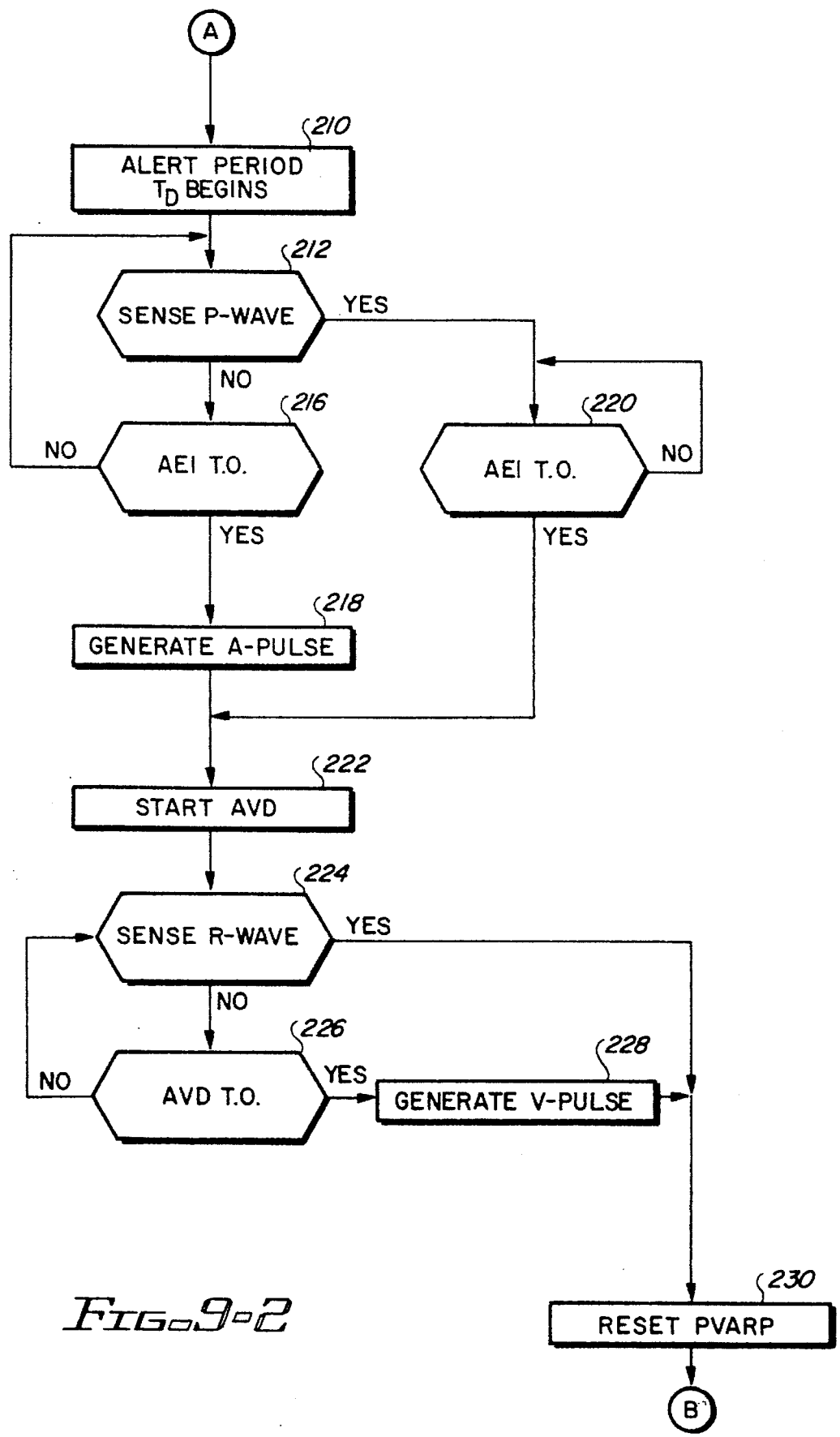

One embodiment of a method that may be used by the control system 26 (FIG. 2) of the present invention to achieve the results shown in FIGS. 6, 7 and 8 is illustrated in the flow chart of FIGS. 9-1 and 9-2. It is noted that each main step of the method shown in FIGS. 9-1 and 9-2 is represented by a box or block, with a reference numeral being assigned to each block. Such steps can be readily carried out by those of skill in the art using a pacemaker controlled by a microprocessor, as described below, or controlled by appropriately designed state logic, as also described below. It is also noted that FIGS. 9-1 and 9-2 show the same flow chart, with different portions of the method being shown in FIG. 9-1 and other portions being shown in FIG. 9-2.

As seen in FIG. 9-1, after starting the method (block 178), an initial step involves loading the programmable control parameters that are used by the pacemaker as the method is carried out (block 180). Such control parameters are downloaded to the memory of the pacemaker in conventional manner. Such parameters include, in addition to the normal parameters used during DDI pacing (such as the initial vales of the PVARP, AEI and AVD), the values of the reference interval $T_B$; the number of pacing cycles n that must have a PVI greater than $T_B$ before a PMRR is detected; the extended PVARP, $T_C$; and the alert interval, $T_D$. Such parameters also include a suitable code that identifies the mode of operation of the pacemaker, as well as a flag that indicates whether, when operating in the DDI mode of operation, the PMRR detection feature of the invention is programmed ON or OFF.

Once all of the operating control parameters have been downloaded, a decision is made as to whether the PMRR detection feature is programmed ON (block 182). If not, then the pacer is operated in its programmed mode (block 184), whatever that mode may be, e.g., DDD pacing, VVI pacing, etc. On a regular basis, a determination is made as to whether such pacing mode is to continue (block 186). If not, then the method stops or terminates (block 188). If so, then a determination is again made as to whether the PMRR option has been programmed ON (block 182).

If the PMRR option is ON (block 182), then the DDI pacing cycle begins (block 190). This means that the AEI and the PVARP are both started at this time. Such pacing cycle, as described above, commences with a ventricular event and concludes with a ventricular event, with the basic pacing interval being defined by the duration of the AEI plus the AVD (when no R-wave is sensed), or the duration of AEI plus a time interval $AVD_S$ (when an R-wave is sensed). During the pacing cycle, the length of PVI is measured (block 192).

Once the PVI is measured, it is compared to the reference interval $T_B$ (block 194). If the PVI is less than $T_B$ (NO branch of block 194), then the next pacing cycle is started and the process repeats (blocks 182, 190, 192). If the PVI is greater than $T_B$ (YES branch of block 194), then a determination is made as to whether n cycles having a PVI greater than $T_B$ must exist before a PMRR determination is made (block 196). If so (YES branch of block 196), then a determination is made as to how many such cycles have occurred (block 198). If n such cycles have not occurred (NO branch of block 198), then the next pacing cycle is started and the process repeats (blocks 182, 190, 192, 194, 196). If n such cycles have occurred (YES branch of block 198), each having its PVI greater than $T_B$ (as determined during each pass through the cycle at block 194), then a PMRR is deemed to have been detected. Note that a PMRR may also be detected if only a single PVI is required to detect a PMRR (NO branch of block 196).

Once a PMRR has been detected, i.e., through the occurrence of a single PVI greater than $T_B$ when only one such PVI is required (NO branch of block 196), or when the PVI's of n consecutive cycles each have a PVI greater than $T_B$ (YES branch of block 198), or when other criteria related to the measured PVI is established, e.g., the average of n PVI's is greater than $T_B$, then the method extends PVARP by the amount $T_E$ to its extended value, $T_C$ (block 200).

Even though a P-wave that occurs during the PVARP is not recognized as a legitimate P-wave, a P-wave that occurs during the $T_E$ portion of the PVARP may still be sensed (block 202). If a P-wave is sensed during this $T_E$ time (YES branch of block 202), then a determination is made as to how much time remains in the current cardiac cycle until the end of the AEI (block 204). If such remaining time is less than a prescribed minimum time (YES branch of block 206), then the AEI is extended by an amount $T_F$ (block 208) in order to assure that the refractory period following the sensed P-wave has ended before the next A-pulse is generated (thereby assuring that such A-pulse will capture the atria).

After the AEI has been extended (block 208), or in the event the P-wave-to-$AEI_{END}$ time (determined at block 204) is greater than the prescribed minimum (NO branch of block 206), or in the event no P-wave is sensed during the extended portion $T_E$ of the extended PVARP (NO branch of block 202), then the alert period, $T_D$, begins (block 210, FIG. 9-2). During $T_D$, which lasts until the end of the AEI, the atrial channel is monitored to determine if a P-wave is sensed (block 212). If a P-wave is not sensed (NO branch of block 212), and if the AEI has timed out (block 216), then an A-pulse is generated (block 218).

After an A-pulse is generated (block 218), or if a P-wave is sensed (YES branch of block 212), and the AEI has timed out (block 220), then the AVD is started (block 222). If an R-wave is sensed during the timing out of the AVD (YES branch of block 224), the PVARP is reset to its non-extended value (block 230), and the next cycle begins (beginning at block 182, FIG. 9-1). If no R-wave is sensed (NO branch of block 224) before the timing out of the AVD (block 226), then a V-pulse is generated (block 228), and the PVARP is reset to its non-extended value (block 230), and the next cycle begins (beginning at block 182, FIG. 9-1).

Turning next to FIG. 10, a simplified timing waveform diagram is shown that illustrates a variation of the present invention. In the previous descriptions, P-waves that occur during PVARP are not sensed. In accordance with the variation shown in FIG. 10, however, this absolute restriction against sensing P-waves during PVARP is modified. As seen in FIG. 10, PVARP is divided into two portions: an absolute refractory portion labeled "ABS", and a relative refractory portion, labeled "REL". No sensing of P-waves occurs during the absolute portion of PVARP. However, any P-wave that occurs during the relative portion of PVARP is sensed and is presumed to be a retrograde P-wave, $P_R$.

Still referring to FIG. 10, should a retrograde P-wave $P_R$ be sensed, i.e., should a P-wave occur during the relative refractory portion of PVARP, then an A-pulse 175 is generated a fixed delay, $T_G$, thereafter. Typically, $T_G$ will be set to the same value, or a similar value, as $T_B$, e.g., 300 msec. Such a value assures that the A-pulse will not be delivered to the atria while they are still refractory following the retrograde P-wave, $P_R$, thereby helping to assure the A-pulse is able to capture the atria, thereby effectively terminating any PMRR that might otherwise be established by the occurrence of the retrograde P-wave, $P_R$.

As a further variation to that which is shown in FIG. 10, rather than generating the A-pulse 175 after the $T_G$ delay following a sensed retrograde P-wave (i.e., a P-wave that occurs during the relative refractory portion of the PVARP), it is also possible to wait until N consecutive retrograde P-waves have been so sensed before the A-pulse 175 is generated. Such action thus requires more than just a single retrograde P-wave before altering the pacing rhythm. The value of N may be a programmable value ranging from, e.g., 2 to 10.

Thus, as seen in FIG. 10, a P-wave that occurs during the latter portion of PVARP is presumed to be a retrograde P-wave. As such, steps are taken (an A-pulse is generated) to immediately change the pacing rhythm so as to prevent any PMRR from developing as a result of the presumed retrograde P-wave(s). In contrast, in FIGS. 6–8 above, P-waves that occur soon after PVARP, under conditions that suggest that a PMRR is present, are presumed to be retrograde P-waves. The continued sensing of such retrograde P-waves is then blocked (by extending PVARP), thereby altering the pacing rhythm, and thereby further breaking the PMRR.

Thus, in the manner described above, the pacemaker of the present invention, when programmed to operate in a DDI mode, detects a PMRR and automatically responds to such PMRR by modifying the DDI operation in a way that terminates the PMRR. More particularly, it is seen that in one embodiment (FIG. 10) the pacemaker immediately alters the pacing rhythm upon detecting a retrograde P-wave by pacing in the atrium so as to prevent the next ventricular event from causing another retrograde P-wave. In another embodiment, it is seen that the pacemaker extends the post-ventricular atrial refractory period (PVARP) upon detection (confirmation) of a PMRR. This action advantageously prevents detection of any retrograde P-waves that may occur in the next pacing cycle. Such PVARP extension is followed by an alert period. If no P-waves are sensed during the alert period, the pacemaker paces in the atrium, thereby preventing the next ventricular event from causing a retrograde P-wave. Advantageously, the AEI is extended, when necessary, to assure a minimum time interval between the sensing of a P-wave and such pacing in the atrium, i.e., the next A-pulse. Such AEI extension assures such A-pulse will not be delivered to the atria while they are still refractory following the P-wave, thereby helping to assure the A-pulse is able to capture the atria. Such action serves to effectively terminate the PMRR.

Microprocessor-Based Control System

The above-described invention may be carried out using any type of implantable pacemaker which can be programmed, or operated, in the manner depicted in the timing waveform diagrams of FIGS. 6–8, or 10, and/or as shown following the steps, or equivalent steps, illustrated in the flow chart of FIGS. 9-1 and 9-2. A preferred type of pacemaker 10 (FIG. 2) to use with the present invention is a rate-responsive microprocessor-based pacemaker 10, as shown in FIGS. 11–14. FIG. 11 depicts a block diagram of the various hardware assemblies and subassemblies used within the rate-responsive microprocessor-based pacemaker 10. As seen in FIG. 11, the pacemaker 10 is made up of a hybrid assembly 300, a pacer subassembly 350, and a pacer assembly 390. The hybrid assembly 300 includes almost all of the electronic circuitry and components of the pacemaker 10. Such circuitry and components include a communication coil 402, a sensor(s) 408 (which typically comprises a piezoelectric crystal used as an accelerometer), and a hybrid integrated circuit 310. The hybrid assembly 300 is combined with a battery 406 and feedthru connectors 320 to form the pacer subassembly 350. All of the elements of the pacer subassembly 350 are housed in, or mounted to, a case 400 (FIG. 12) which is hermetically sealed. Electrical connection is made with the circuits sealed inside of the pacer subassembly 350 by way of the feedthru connectors 320. Such feedthru connectors 320 are then connected to the lead connector 13, attached to the pacer subassembly 350, in order to form the completed pacer assembly 390. The completed pacer assembly 390, when suitable pacing/sensing leads 14 and 16 (FIG. 2) are attached thereto through the connector 13, forms a functional pacemaker.

Figure 12:
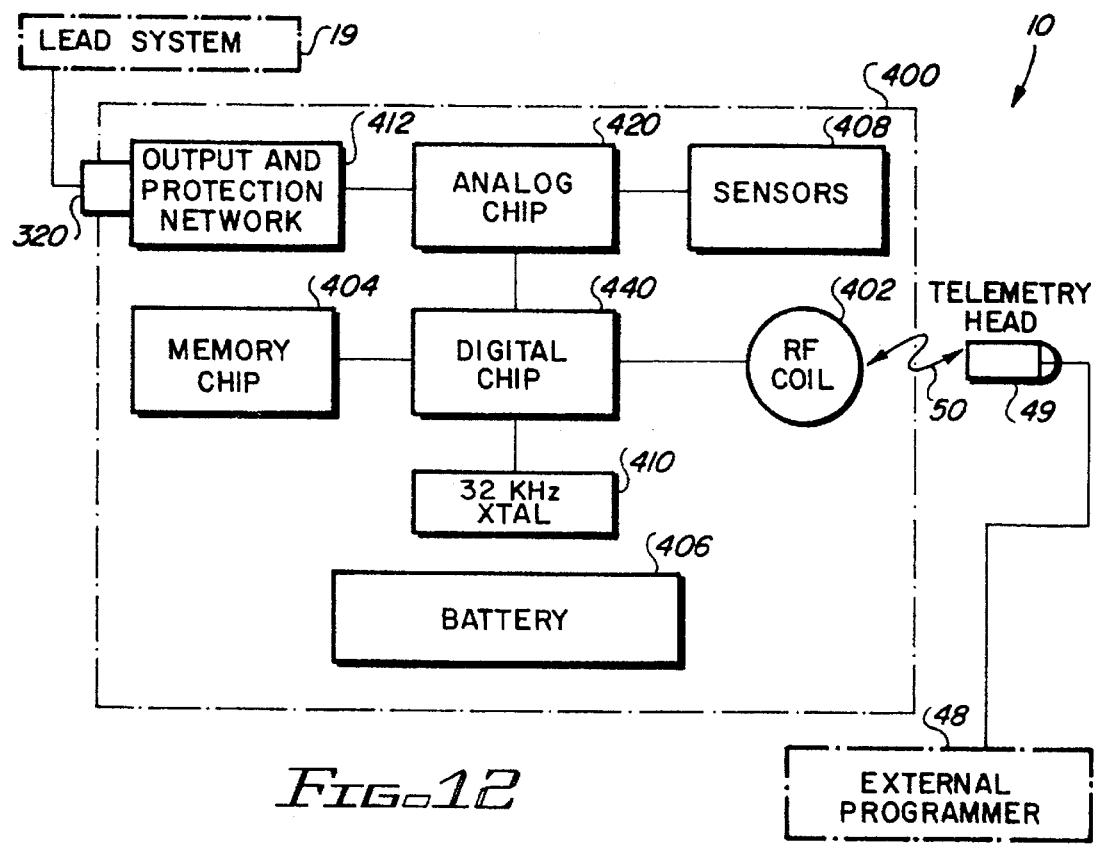
FIG. 12 is a block diagram of the hybrid assembly shown in FIG. 11.

Referring next to FIG. 12, a more detailed block diagram of the pacemaker 10, and particularly the pacer subassembly 350, is shown. As seen in FIG. 12, the pacemaker 10 and a lead system 19 (which lead system 19 comprises the leads 14 and 16, and the connector 13) are used with (i.e., programmed by and/or monitored with) the external programmer 48 (FIG. 2). The lead system 19 may also include an oxygen sensor lead, which lead contains a light emitting diode (LED) detector assembly used to measure the oxygen content of the blood. Such a lead is described, e.g., in U.S. Pat. No. 4,815,469, incorporated herein by reference.

The external programmer 48 includes a telemetry head 49 that is positioned proximate the implantable pacemaker 10 whenever a communication link 50 is to be established between the pacemaker 10 and the external programmer 48. The external programmer may be of conventional design, as described, e.g., in U.S. Pat. No. 4,809,697, incorporated herein by reference.

The components of the pacer subassembly 350 are housed within a suitable sealed case or housing 400 (which case or housing is represented in FIG. 12 by the dashed line 400). The case 400 is preferably a titanium metal case. The components within the case 400 include an RF coil 402, a memory chip 404, a battery 406, one or more physiological or other sensors in a sensor circuit 408, a crystal 410, an output/protection network 412, an analog chip 420 and a digital chip 440.

The battery 406, which is by volume the largest component within the pacer subassembly 350, may be of conventional design, and is generally a lithium battery that provides operating power to all of the electronic circuits within the pacer subassembly. The RF coil 402 is used to establish the communication link 50 with the telemetry head 49. The crystal 410 is used in conjunction with a crystal oscillator circuit on the digital chip 440 (described below) to provide a stable clock frequency for the pacemaker circuits. In the preferred embodiment, the frequency of the crystal oscillator is 32 KHz, although any suitable frequency could be used. The sensor circuit 408 includes appropriate sensors used by the pacemaker as it carries out a rate-responsive pacing function. For example, in one embodiment, the sensor circuit 408 includes an accelerometer adapted to sense patient activity.

The memory chip 404 may be any suitable type of memory device wherein data may be stored and retrieved. Preferably the memory chip 404 is a low-power static random access memory (SRAM) chip wherein the operating parameters, e.g., control variables, of the pacemaker may be stored, and wherein sensed data may be stored, as required. The analog chip 420 and the digital chip 440 contain the main processing and control circuits of the pacemaker. These chips are advantageously designed to minimize the number of components needed external thereto for operation of the pacemaker. The analog chip 420 interfaces with the lead system 19 through the output and protection network 412 and the feedthru connectors 320. The network 412 includes, e.g., output coupling capacitors and circuits which protect the analog chip 420 from high static or other voltages that might be coupled to the lead system 19, as are commonly used in implantable medical devices. The feedthru connectors 320 allow electrical connection through the hermetically sealed case 400, and may be of conventional design.

Figure 13:
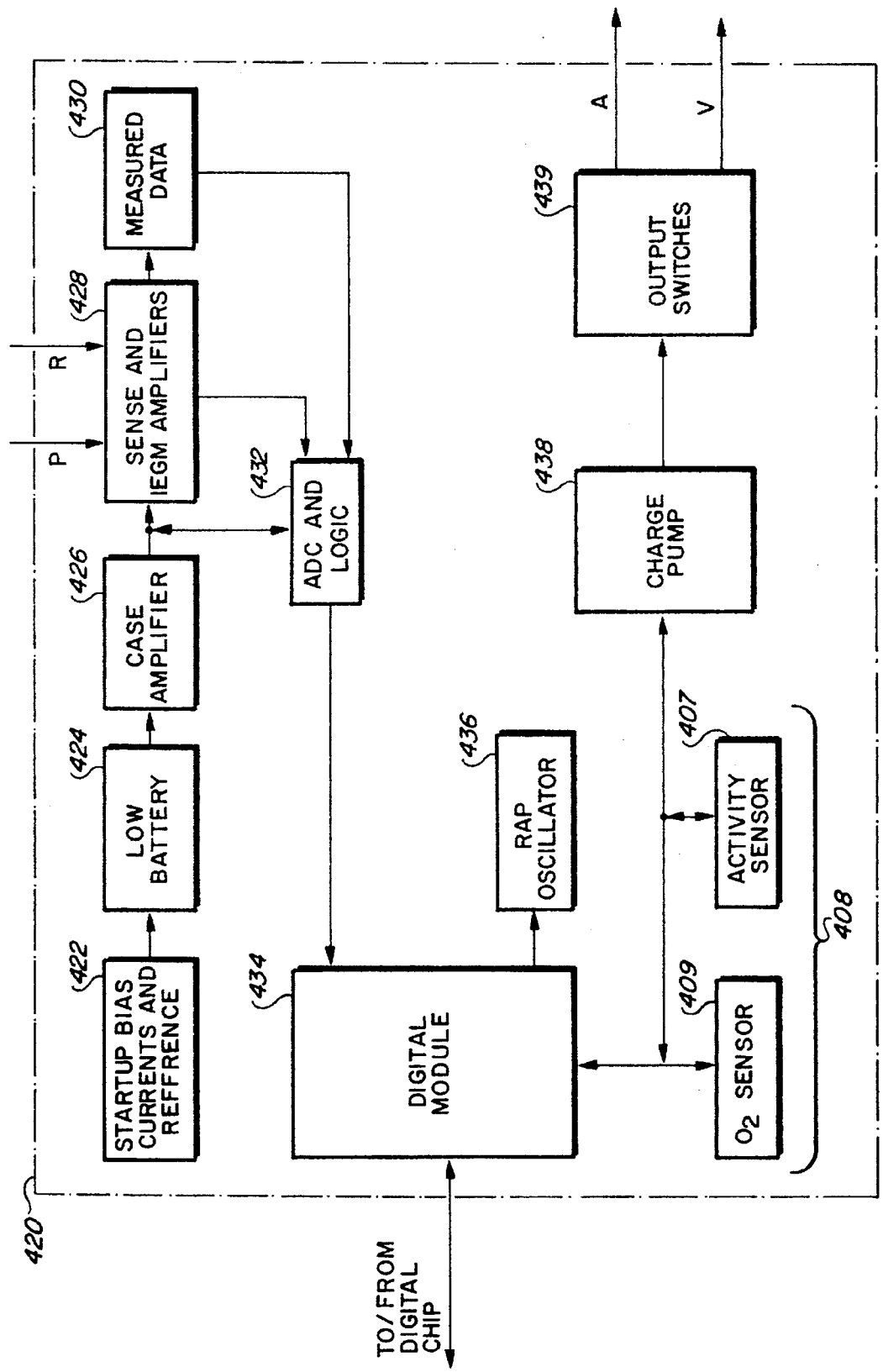
FIG. 13 is a block diagram of the analog chip portion of the hybrid assembly shown in FIG. 12.

Referring next to FIG. 13, a block diagram of the analog chip 420 is shown. The analog chip contains all the necessary sub-systems and modules to interface to the lead system 19 and the digital chip 440. For example, a startup/bias-current/reference module 422 contains the power-up signals used to initialize the pacer circuit when the battery is first applied. A low battery module 424 detects four voltage levels of the battery voltage for determining the battery status. A case amplifier 426 generates a CASE bias voltage that is used as a reference for the sense and IEGM (intracardiac electrogram) amplifier module 428. The sense and IEGM amplifier module 428 includes the P-wave amplifier 22 and the R-wave amplifier 24, described in FIG. 2. A measured data module 430 measures the battery voltage and current and other analog parameters of the pacing system. An ADC and Logic module 432 includes an analog-to-digital converter (ADC) and timing logic that are used to convert the analog signals of the pacemaker to 8-bit digital words. These digital words are then passed to a digital module 434, which module is used to generate all the basic timing and bus control functions as data is passed back and forth between the analog chip 420 and the digital chip 440.

Still referring to FIG. 13, it is seen that a Runaway Protection (RAP) circuit oscillator 436 is also coupled to the Digital Module 434. Such oscillator 436 provides an independent time base for limiting the highest pacing rate allowed by the pacemaker. Further coupled to the digital module 434 is the sensor network 408 (also referred to as the sensor circuit 408). The sensor network 408 includes appropriate sensors for sensing activity and other parameters. For example, an 02 sensor circuit 409 may be used in conjunction with the oxygen sensor lead, when used, to measure blood oxygen of the patient. An activity sensor 407 may also be used to sense patient activity as measured, e.g., by an accelerometer. A charge pump circuit 438 generates the output voltages for the stimulation pulses that are delivered to the patient's heart. A network of output switches 439 connects the charge developed by the pump circuit 438 to the output leads at the appropriate time to form the appropriate stimulation pulses.

It is thus seen that the analog chip 420 contains the necessary circuitry to sense and detect atrial or ventricular events, digitize IEGM waveforms, measured data and other various analog signals, and provide such sensed and digitized signals to the digital module 434 for use by the digital chip 440. The charge pump circuit 438 acts as a voltage doubler/tripler for high output pulse capability. The output pulse width is controlled by the output switches 439. The condition of the battery is monitored, and independent Runaway Protection is provided.

Figure 14:
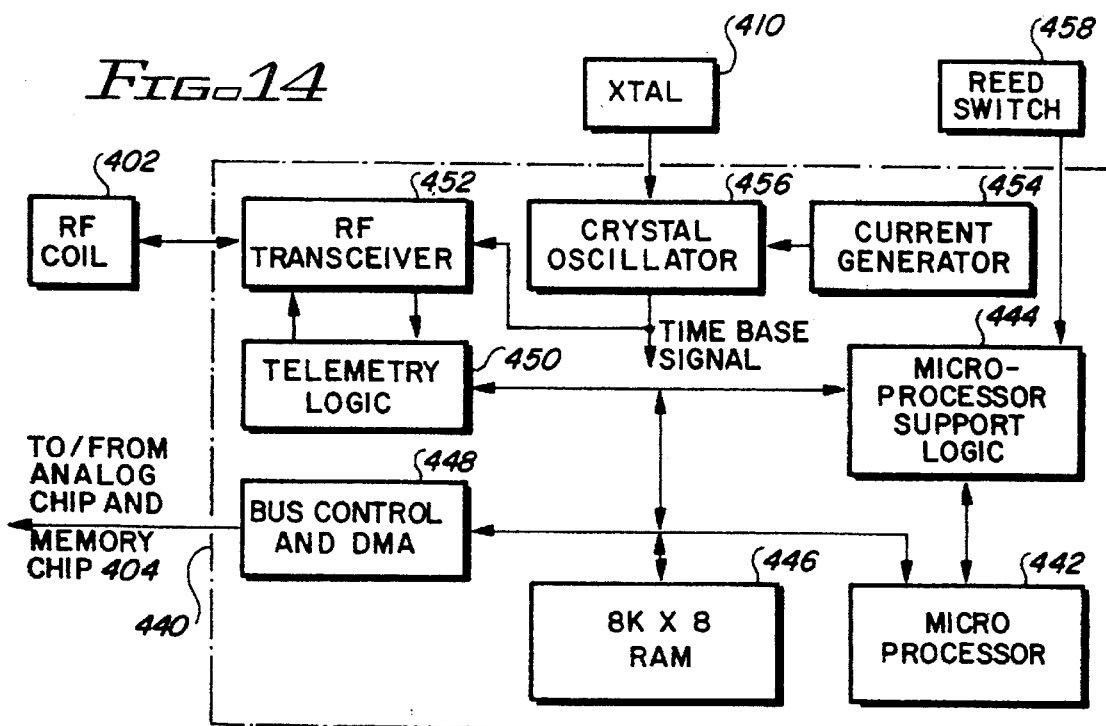
FIG. 14 is a block diagram of the digital chip portion of the hybrid assembly shown in FIG. 12, and illustrates the use of a microprocessor to control the operation of the pacemaker.

Turning next to FIG. 14, it is seen that the main control element of the pacemaker is a microprocessor 442, which microprocessor is included within the digital chip 440. The digital chip 440 contains all the necessary logic to interface the analog chip 420 with the internal microprocessor 442. The microprocessor 442 includes a basic CPU (central processing unit). In addition, an 8K by 8 static random access memory (SRAM) 446, or equivalent memory element, is connected to the microprocessor 442 to store data and programs. Microprocessor support logic 444, also coupled to the microprocessor 442, includes interrupt logic, timer logic, noise/sensed event logic, and magnet status logic. A bus controller 448 is further included on the digital chip 440 to provide direct memory access (DMA) timing and control of data transfer with the analog chip 420, and the memory chip 404, including timing and control of the analog-to-digital converter 432 (FIG. 13) and telemetry data. Telemetry logic 450 contains clock logic, IEGM and marker logic, telemetry command protocol logic, telemetry interrupt logic, error checking logic and CPU reset logic. An RF transceiver 452, coupled to the RF coil 402, transmits and receives telemetry data from the external programmer 48 through the telemetry head 49 (see FIG. 12). A crystal oscillator circuit 456, in conjunction with the crystal 410 (external to the digital chip 440) provides a crystal-controlled time base signal for the pacemaker system. A current generator 454 provides the bias currents for the digital chip. A reed switch 458 (external to the digital chip 440) is coupled to the microprocessor support logic 444. The reed switch 458 detects the presence of a magnetic field, which magnetic field is present whenever the telemetry head 49 (FIG. 12) is in place on the patient's skin above the location where the pacemaker is implanted.

The pacemaker architecture and circuitry described in connection with FIGS. 11–14 provides the basic functions of the pacemaker described in connection with FIG. 2, plus other pacing/sensing functions as are known in the art. For purposes of the present invention, the pacemaker circuitry of FIGS. 11–14 sets the basic timing of the pacing interval, including setting the PVARP, AEI and AVD intervals shown in FIGS. 4–5, or as otherwise set as a function of a sensor-indicated-rate (SIR) derived from the sensor circuits 408. The circuitry also provides for generating trigger signals that cause A-pulses and/or V-pulses to be provided, as well as sensing or detecting natural ventricular events (R-waves) and/or natural atrial events (P-waves), as required, in order to operate the pacemaker in a DDI mode and to maintain a cardiac rhythm defined by the AEI and AVD. Further, the circuitry permits the storing of certain reference time intervals, e.g., $T_B$ and $T_E$, and for measuring the time interval between a sensed P-wave and the subsequent V-pulse (PVI) in order to ascertain if the PVI thus measured is greater than $T_B$ for a prescribed number of consecutive cardiac cycles (evidencing the presence of a PMRR). If the presence of a PMRR is thus established, then the circuitry further allows for automatically taking appropriate action, as illustrated in FIGS. 6–8, or 10 to terminate the PMRR. Such action modifies next DDI cycle, as shown in described more fully above, by extending the PVARP by a prescribed amount, e.g., $T_E$ (to produce an extended PVARP equal to $T_C$), and then monitors the heart for P-waves during the alert interval $T_D$ (equal to the time period between the end of the extended PVARP and the end of the AEI) to determine whether an A-pulse should be generated or not at the conclusion of the AEI. Further, other actions, e.g., to maintain a minimum time interval $T_G$ between a P-wave that occurs late in the PVARP, as illustrated in FIGS. 8 or 10, and/or as outlined in the flow chart of FIGS. 9-1 and 9-2, may also be taken by the circuitry of FIGS. 11–14.

Advantageously, use of the microprocessor-based pacemaker 10 as shown in FIGS. 2 and 11–14 permits a great deal of flexibility in how the present invention is implemented and carried out. For example, all of the time interval values associated with the invention, e.g., AVI, AVD, PVI, $T_B$, $T_E$, and the minimum P-to-AEI$_{END}$, may easily be altered, as required, to suit the needs of a particular patient.

State-Machine-Based Control system

As an alternative to the microprocessor-based pacemaker described in connection with FIGS. 11–14, the present invention may also be practiced using a state-machine-controlled pacemaker. In a state-machine-controlled pacemaker, the control system 26 (FIG. 2) is implemented using a state machine circuit. An example of a state machine control circuit 26 is illustrated in FIG. 3. In accordance with state machine operation, and with reference to FIG. 3, a set of state registers 60 define the particular state of the pacer at any instant in time. In general, and as an overview of state machine operation, each state, by design, causes a certain activity or function to be carried out. Several states are executed in a sequence during a given pacing cycle. The sequence of states that is executed in a particular cardiac or pacing cycle is determined by the particular events that occur, such as the sensing of a P-wave or an R-wave, as well as the current state, as certain states can only be entered from certain other states. Only one state can exist at any instant of time, although several different state machines (or control systems) may operate in parallel to control diverse functions. For example, the telemetry circuit 44 (FIG. 2) may utilizes its own state machine, such as is described in the above-cited patent, or its own control microprocessor. When used, such telemetry circuit state machine or microprocessor operates essentially independent of the control system state machine of FIG. 3.

At the heart of the control system 26 of FIG. 3 is the state logic 62. It is the state logic that controls the "state" of the state registers 60, and hence the function or operation that will next be carried out by the system. The state logic is thus designed to carry out the functions of the invention as described below in connection with FIGS. 6–8. The state logic 62 receives as inputs the current state of the state registers, made available over a state bus 64 (which state bus directs the state of the system to several sections of the control system), as well as other signals indicating the current status of the system or events that have occurred. The output signal 28 from the P-AMP 22 and the output signal 30 from the R-AMP 24 (FIG. 2) are directed to an input decode logic circuit 66. This circuit generates appropriate logic signals "IPW" (Inhibiting P-wave) and "IRW" (Inhibiting R-wave) that are selected by a multiplexer 68 and sent to rate-determining logic 70. These signals are also sent to the state logic 62. The function of the rate-determining logic 70 is to determine the rate at which either the IPW or IRW signals are occurring. A signal representative of this rate is sent, as an output signal from the rate determining logic 70, to the state logic 62 over signal line 72. Rate-determining logic 70 further receives a sensor rate signal 54 from the sensor 52 (FIG. 2), and (depending upon the particular state of the system, as defined by the state registers 60, and as made available to the rate-determining logic 70 over the state bus 64) sends a rate signal to the state logic 62 over signal line 72 indicative of this sensor rate.

Still referring to FIG. 3, a memory control circuit 74 provides the needed interface between the circuits of the control system 26 and the memory 40 (FIG. 2). This memory control circuit may be any conventional memory access circuit that sends or receives data to or from memory at a specified address. Data retrieved from memory 40 may be sent to either the state logic 62 (over signal line(s) 75) or to one or more programmable timers 76 (over signal line(s) 77). Data sent to memory 40 may be either the current state of the system (obtained off of the state bus 64), or other selected signals from the state logic (as made available over signal line(s) 73). The function of the programmable timer(s) 76 is to define a prescribed time interval, the length of which is set by the signal(s) received from the memory control 74 over signal line(s) 77, and the starting point of which begins coincident with the start of the current state, as obtained from the state bus 64. The timer 76 further generates a time-out (T.O.) signal when this prescribed time interval has elapsed. During this prescribed time interval, the timing function may be reset by a reset signal, typically obtained from the input decode logic 66, although some states (as obtained from the state bus 64) may also effectuate an immediate reset of the timer 76. The time-out signal is sent to time-out decode logic 78. It is the function of the time-out decode logic to generate the appropriate trigger signals that are sent to the A-PG 18 or the V-PG 20 (FIG. 2). Further, an appropriate logic signal(s) is sent to the state logic 62 by the time-out decode logic 78 over signal line(s) 80 in order to notify the state logic that the respective trigger signals have been generated.

An oscillator 82, preferably a crystal-controlled oscillator, generates a basic clock signal CO that controls the operation of the system logic. This clock signal CO is sent to clock logic circuits 84, where other appropriate clock signals, such as clock signals C1, C2, and C3, are generated, all derived from the basic clock signal CO. These clock signals are distributed throughout the control system 26 in order to appropriately synchronize the various events and state changes that occur within the pacemaker. The rate of the basic clock signal CO is not critical to the present invention. In general, a rate of 25–40 KHz for the basic clock rate CO is adequate. This rate provides a basic time increment of 25–40 microseconds each clock cycle, and this is more than enough time to effectively control the pacemaker operation. If desired, a faster basic clock rate can be used, particularly by the memory control 74, to speed up the data transfer between the control system 26 and the memory 40, although for most pacemaker operations, a fast data transfer rate is not essential.

In operation, the control system of FIG. 3 starts at an initial state, wherein the state registers 60 assume a prescribed value that defines the initial state. For example, assuming four flip flops are used for the state registers 60, an initial state might be "1000" (hexadecimal "8") wherein the first flip flop assumes a "1" state, and the remaining three flip flops each assume a "0" state. This state may be defined as an atrial escape interval (AEI) state wherein a prescribed AEI or delay is initiated. As soon as the memory control 74 detects that the AEI state has been initiated, as evidenced by the "1000" appearing on the state bus 64, it retrieves from the memory 40 an appropriate data word, previously programmed into the memory 40 from the external programmer 48, that defines the desired length of the AEI. This data word is sent to one of the programmable timers and sets the length of the time period that is to be measured during the AEI state.

The timer 76 is essentially just a counter that counts down (or counts up), using a specified clock signal, to the value specified in the data word. When the counting has been completed, and assuming that the counter has not been reset by the sensing of a P-wave or an R-wave (depending upon the mode of operation of the pacer), the counter or timer 76 is said to have "timed out", and an appropriate time-out signal is generated that is sent to the time-out decode logic 78. (Other types of timers may, of course, also be used, such as are known in the art, including capacitor timing circuits.) The decode logic, in turn, recognizes that the current state of the system is the AEI state (as determined by monitoring the state bus 64), and therefore that the AEI (atrial escape interval) has timed-out without any cardiac activity having been sensed. Having made this determination, the decode logic generates an A-pulse trigger signal, sent to the A-PG 18, so that the atrium can be stimulated with an A-pulse. At the same time, an appropriate logic signal(s) is sent to the state logic 62 over the signal line(s) 80 to alert the state logic to the fact that one of the timers 76 has timed-out.

The state logic 62, in response to receiving the signal(s) from the time-out decode logic 78, and also in response to the current AEI state, triggers the next state of the prescribed sequence. For most dual-chamber pacing modes, e.g., DDD operation, this state is typically a blanking state, or BLANK state, during which the P and R sense amplifiers, 22 and 24, are disabled. Accordingly, the state logic generates appropriate signal(s) on signal lines 36 and 38 to blank the P-wave sense amplifier 22 and the R-wave sense amplifier 24, and also causes the state registers 60 to change to a BLANK state, which state could be defined, for example, by the flip flops of the state registers 62 assuming a "0001" (hex "1") condition. This BLANK state, detected on the state bus 64, causes the memory control circuitry to retrieve an appropriate data word from memory that defines the length of the blanking interval, which data word is loaded into one of the programmable timers 76. As soon as the appropriate timer 76 times out, indicating that the prescribed blanking interval has elapsed, a time-out signal is generated that is sent to the time-out decode logic 78. Upon receipt of this time-out signal, and in response to the current state being a BLANK state, the time-out decode logic 78 sends an appropriate logic signal to the state logic 62. The state logic 62 responds by steering the state registers 62 to assume the next state in the prescribed sequence, which may be, for example, an A-V Delay (AVD) state.

At the beginning of the AVD state, another value is loaded into one of the programmable timers 76 that defines the length of the A-V interval or delay. If the appropriate timer 76 times out without being reset, indicating that no P-waves or R-waves have been sensed, the decode logic generates a V-trigger signal, and notifies the state logic 62 of this event. The state logic, in turn, causes the next appropriate state to be entered, which state may be another blanking state, or BLANK state, similar to the one described above, but having perhaps a different duration. At the conclusion or timing out of this second BLANK state, the next state in the prescribed sequence is initiated, which state may be a post-ventricular atrial refractory period (PVARP) state.

In the manner described above, the control system 26 assumes one state after another, thereby controlling the operation of the pacemaker. In general, a state is changed when an appropriate one of the timers 76 times out, or when a prescribed event occurs. For example, if during the AEI state an IPW signal is received (indicating that a P-wave has been sensed), the input decode logic 66 responds appropriately for the given pacing mode. If the pacing mode is a DDD mode, a reset signal is generated to reset the timer 76, and the state logic 62 responds by immediately (e.g., within the next few clock cycles) changing the state to the next appropriate state, e.g., an AVD state. If the pacing mode is a conventional DDI mode, the timer 76 is not reset. However, the fact that a P-wave occurred is noted so that the generation of an A-pulse at the conclusion of the AEI will be inhibited, as the AVD state begins. Further, if during the AVD state an IRW signal is received (indicating that an R-wave has been sensed), the input decode logic 66 generates another reset signal to reset an appropriate one of the timers 76, and the state logic responds by immediately changing the state to the next appropriate state, e.g., a PVARP state and/or an AEI state. It is noted that the state of the control system could also be changed by receipt of an appropriate command from the telemetry system.

The control system 26 of FIG. 3 may be realized using dedicated hardware circuits, or by using a combination of hardware and software (or firmware) circuits. The appropriate sequence of states for a given mode of operation, such as DDD or DDI, for example, can be defined by appropriate control of the memory control 74 and the state logic 62. These circuit elements, in turn, are most easily controlled through an appropriate software or firmware program that is placed or programmed into the pacemaker memory circuits. The manner of accomplishing such programming is known in the art.

While the invention herein disclosed has been described by means of specific embodiments and applications thereof, numerous modifications and variations could be made thereto by those skilled in the art without departing from the scope of the invention set forth in the claims.

What is claimed is:

1. A dual-chamber implantable pacemaker comprising:

sensing means for sensing an atrial depolarization (P-wave) and a ventricular depolarization (R-wave) within a cardiac cycle;

pulse generator means for generating an atrial stimulation pulse (A-pulse) and a ventricular stimulation pulse (V-pulse);

control means for controlling the sensing means and pulse generator means so as to operate said pacemaker in a DDI mode of operation, said DDI mode of operation having a pacing period defined by a sequence that comprises an atrial escape interval (AEI) followed by an A-V delay (AVD), with the AEI being of a preset duration, and the AVD having a preset maximum duration, after which a V-pulse is generated, but being shortened with no V-pulse being generated in the event an R-wave is sensed, and wherein the duration of the pacing period is not altered by the sensing of a P-wave, whereby P-wave tracking does not occur;

detection means for detecting a pacemaker mediated retrograde rhythm (PMRR) comprising
means for measuring a P-to-V time interval (PVI) associated with at least one DDI pacing period, said PVI comprising the time interval between the sensing of a P-wave by said sensing means and the generation of a V-pulse by said pulse generating means, and comparison means for comparing the measured PVI to a reference interval and detecting a PMRR whenever the measured PVI exceeds the reference interval; and modifying means responsive to the detection of a PMRR by said detection means for automatically modifying said control means so as to provide a modified DDI response to terminate the detected PMRR.

2. The dual-chamber pacemaker of claim 1, wherein the means for measuring a PVI of said PMRR detection means comprises means for measuring the PVI associated with n consecutive DDI pacing periods, where n is an integer of at least 4, and wherein the comparison means of said PMRR detection means comprises means for comparing the measured PVI of each of said n consecutive DDI pacing cycles to the reference interval and detecting a PMRR only when the measured PVI of each of said n consecutive DDI pacing cycles exceeds the reference interval.

3. The dual-chamber pacemaker of claim 1, wherein the means for measuring a PVI of said PMRR detection means comprises means for measuring the PVI associated with n consecutive DDI pacing periods, where n is an integer of at least 4, and wherein the comparison means of said PMRR detection means comprises means for computing an average PVI for the measured PVIs of the n consecutive DDI pacing cycles, and comparing the average PVI to the reference interval, and detecting a PMRR only when the average PVI exceeds the reference interval.

4. The dual-chamber pacemaker of claim 1, wherein said reference interval comprises an interval $T_B$ having a duration within the range of 250 to 350 msec.

5. The dual-chamber pacemaker of claim 4, wherein said interval $T_B$ has a duration of about 300 msec.

6. The dual-chamber pacemaker of claim 1, wherein said control means includes means for generating a post-ventricular atrial refractory period (PVARP) that starts to time-out coincident with the beginning of the AEI, said PVARP being of a shorter duration than said AEI, and disabling means for disabling the sensing means during the timing out of said PVARP; and wherein said modifying means includes:

means for extending said PVARP in response to said detection means detecting a PMRR;

means for beginning an alert time period, $T_{ALERT}$, after the extended PVARP has timed-out; and means for triggering said pulse generator means to generate an A-pulse at the conclusion of the AEI if no P-wave is sensed during the $T_{ALERT}$ time period, and for not triggering said pulse generator, and thereby inhibiting the generation of an A-pulse, at the conclusion of the AEI if a P-wave is sensed during the $T_{ALERT}$ time period.

7. The dual-chamber pacemaker of claim 6, wherein said means for extending said PVARP extends the PVARP to an interval of about 500 msec.

8. The dual-chamber pacemaker of claim 6, wherein said $T_{ALERT}$ interval comprises an interval that begins at the conclusion of the extended PVARP and that ends upon the timing out of the AEI.

9. The dual-chamber pacemaker of claim 1, wherein the control means further includes means for generating a post ventricular atrial refractory period (PVARP) that is divided into an absolute refractory first portion and a relative refractory second portion, and wherein the detection means for detecting a PMRR includes means for sensing a P-wave during the relative refractory second portion of the PVARP, and wherein the modifying means comprises means for generating an A-pulse a fixed delay after sensing a P-wave during the relative refractory second portion of the PVARP.

10. The dual-chamber pacemaker of claim 9, wherein the modifying means generates the A-pulse only after m P-waves have been detected during the relative refractory second portion of the PVARP in each of m consecutive pacing cycles, where m is an integer greater than one.

11. The dual-chamber pacemaker of claim 9, where m is an integer from two to ten.

12. The dual-chamber pacemaker of claim 9, wherein the fixed delay after which an A-pulse is generated following the sensing of a P-wave during the relative refractory portion of the PVARP comprises approximately 300 msec.

13. A dual-chamber implantable pacemaker comprising:

an atrial channel, said atrial channel including means for sensing a P-wave and means for generating an A-pulse, a ventricular channel, said ventricular channel including means for sensing an R-wave and means for generating a V-pulse, a control system coupled to said atrial and ventricular channels that controls the operation of said atrial and ventricular channels in accordance with a DDI mode of operation, and that detects the occurrence of a pacemaker mediated retrograde rhythm (PMRR), and alters the DDI mode of operation in response to detecting a PMRR in order to terminate the PMRR; and a memory coupled to said control system, said memory including means for storing a set of control parameters that define the DDI mode of operation;

said control system including:

time-interval defining means for defining a set of time intervals as a function of said set of control parameters, said set of time intervals including a post-ventricular atrial refractory period (PVARP), an extended PVARP, an atrial escape interval (AEI), and an A-V delay (AVD), where the PVARP and extended PVARP are less than the AEI, logic circuitry responsive to the time-interval defining means and to the sensed occurrence of P-waves and R-waves that generates a set of control signals that control the operation of said pacemaker so that its operation conforms with the DDI mode of operation, said logic circuitry including means for:

generating a pacing cycle that begins upon the occurrence of a ventricular event and terminates upon the occurrence of a successive ventricular event, where a ventricular event comprises either the sensing of an R-wave or the generating of a V-pulse;

starting the AEI and the PVARP at the beginning of each pacing cycle;

sensing whether a P-wave occurs after the end of the PVARP but prior to the end of the AEI, and if not, generating an A-pulse at the conclusion of the AEI, and if so, inhibiting the generation of an A-pulse at the conclusion of the AEI;

starting the AVD upon the timing out of the AEI, with the AVD terminating upon the earliest occurrence of either the sensing of an R-wave or the timing out of the AVD;

determining if a pacing cycle includes the sensing of a P-wave and the generation of a V-pulse, and if so, measuring the P-to-V interval between the sensed P-wave and the generated V-pulse;

comparing the measured P-to-V interval to a reference interval and generating a PMRR detect signal if the measured P-to-V interval is greater than the reference interval;

extending the PVARP to the extended PVARP in the next pacing cycle following the generation of a PMRR detect signal;

determining if a P-wave is sensed following the extended PVARP but prior to the end of the AEI, and if not, generating an A-pulse at the end of the AEI.

14. The dual-chamber pacemaker of claim 13, wherein the reference interval comprises an interval within the range of about 250 and 350 msec.

15. The dual-chamber pacemaker of claim 14, wherein the reference interval comprises an interval of about 300 msec.

16. The dual-chamber pacemaker of claim 15, wherein the extended PVARP comprises a time period within the range of about 450 to 550 msec.

17. The dual-chamber pacemaker of claim 16, wherein the extended PVARP is a time period of about 500 msec.

18. The dual-chamber pacemaker of claim 13, wherein the means for measuring the P-to-V interval includes means for measuring the P-to-V interval for a predetermined number of pacing cycles; and wherein the means for generating the PMRR detect signal includes means for generating such PMRR detect signal only if the measured P-to-V interval for each of said predetermined number of pacing cycles is greater than the reference interval.

19. The dual-chamber pacemaker of claim 18, wherein the predetermined number of pacing cycles that must each have a P-to-V interval greater than the reference interval before the PMRR detect signal is generated comprises at least four.

20. A method of operating a dual-chamber pacemaker comprising:

(a) sensing when an atrial depolarization (P-wave) and a ventricular depolarization (R-wave) occur within a patient's cardiac cycle;

(b) generating an atrial stimulation pulse (A-pulse) and a ventricular stimulation pulse (V-pulse) in accordance with a DDI mode of operation, said DDI mode of operation having an atrial escape interval (AEI) and an A-V delay (AVD), with the AEI being of a preset duration, and with the AVD having a preset maximum duration, and having a DDI pacing period that is equal to the AEI followed by the AVD, with a V-pulse being generated at the conclusion of the AVD only if an R-wave is not sensed during the AVD, and with the AVD being immediately terminated upon sensing an R-wave, thus ending the DDI pacing period and beginning the next DDI pacing period, whereby the duration of the DDI pacing period is not altered by the sensing of a P-wave, whereby P-wave tracking does not occur;

(c) detecting whether a pacemaker mediated retrograde rhythm (PMRR) occurs during the DDI mode of operation carried out in step (b) by measuring a P-to-V interval that comprises the time interval between the sensing of a P-wave and the generating of a V-pulse within the DDI pacing period, comparing the measured P-to-V interval to a reference interval, and defining a PMRR to be present whenever the measured P-to-V interval exceeds the reference interval; and (d) automatically modifying the DDI operation of step (b), in response to detecting a PMRR in step (c), in order to terminate the PMRR.

21. The method of claim 20, wherein the step of measuring a P-to-V interval carried out as part of step (c) comprises measuring the P-to-V interval of n consecutive DDI pacing periods, where n is an integer of at least four, and computing an average of the n P-to-V intervals thus measured.

22. The method of claim 20, wherein the step detecting whether a PMRR is present includes defining a PMRR to be present only when the P-to-V interval for each of a prescribed number of consecutive DDI pacing periods exceeds the reference interval.

23. The method of claim 20, wherein the step of automatically modifying the DDI operation comprises extending a post-ventricular atrial refractory period (PVARP), used at the beginning of each DDI pacing period to define a time period that is part of the AEI during which P-waves are not sensed, from a normal value to an extended value;

sensing whether a P-wave occurs during an alert period, $T_{ALERT}$, that starts at the conclusion of the extended PVARP and terminates when the AEI terminates; and generating an A-pulse at the conclusion of the AEI if a P-wave is not sensed during the alert period, $T_{AERT}$.

24. A dual-chamber implantable rate-responsive pacemaker comprising:

sensing means for sensing an atrial depolarization (P-wave) and a ventricular depolarization (R-wave) within a cardiac cycle;

pulse generator means for generating an atrial stimulation pulse (A-pulse) and a ventricular stimulation pulse (V-pulse);

a sensor that senses a prescribed physiological parameter that provides some measure of what an appropriate heart rate should be;

control means coupled to said sensor, sensing means, and pulse generator means for controlling the sensing means and pulse generator means so as to operate said rate-responsive pacemaker in a DDI mode of operation, said DDI mode of operation having a pacing period defined by a sequence that comprises an atrial escape interval (AEI) followed by an A-V delay (AVD), with the AEI having a duration that varies as a function of the physiological parameter sensed by said sensor, and with the AVD having a preset maximum duration, after which a V-pulse is generated, and with the AVD being shortened with no V-pulse being generated in the event an R-wave is sensed during the AVD;

detection means for measuring a P-to-V time interval associated with at least one DDI pacing period, said P-to-V time interval comprising the time interval between the sensing of a P-wave by said sensing means and the generation of a V-pulse by said pulse generating means;

comparison means for comparing the measured P-to-V time interval to a reference interval and generating a pacemaker mediated retrograde rhythm (PMRR) detect signal whenever the measured P-to-V time interval exceeds the reference interval; and modifying means responsive to said PMRR detect signal for automatically modifying said control means so as to provide a modified DDI response to terminate said PMRR, said modified DDI response including extending said AEI by an amount sufficient to assure that at least a prescribed interval of time exists between the detection of a P-wave during the AEI and the end of the AEI.

25. The dual-chamber pacemaker of claim 24, wherein said prescribed interval of time comprises a fixed time period that is at least as long as a natural refractory period following a P-wave.

26. The dual-chamber pacemaker of claim 25, wherein said fixed time period comprises a time period of at least 300 msec, whereby at least 300 msec will always exist between the sensing of a P-wave and the generating of an A-pulse at the conclusion of the AEI, which 300 msec assures that the A-pulse is not delivered to a patient's heart at a time when the atria of the heart are still refractory.

27. The dual-chamber pacemaker of claim 25, wherein said control means includes means for generating a post-ventricular atrial refractory period (PVARP) that starts to time-out coincident with the beginning of the timing out of the AEI, said PVARP being of a shorter duration than said AEI, and means for disabling the sensing means during the timing out of said PVARP; and wherein said modifying means includes:

means for extending said PVARP in response to said PMRR detect signal; and means for triggering said pulse generator means to generate an A-pulse at the conclusion of the AEI if no P-wave is sensed during an alert period, $T_{ALERT}$, that begins at the conclusion of the extended PVARP and terminates at the conclusion of the AEI, and for not triggering said pulse generator, and thereby inhibiting the generation of an A-pulse, at the conclusion of the AEI if a P-wave is sensed during the alert period, $T_{ALERT}$.

28. The dual-chamber pacemaker of claim 27, wherein said means for extending said PVARP extends the PVARP to an interval of about 500 msec.

29. The dual-chamber pacemaker of claim 28, wherein said detection means includes means for measuring the P-to-V time interval associated with n consecutive DDI pacing periods, where n is an integer of at least four, and wherein the comparison means comprises means for comparing the measured P-to-V time interval associated with each of the n consecutive DDI pacing periods to the reference interval and generating the PMRR detect signal only if each measured P-to-V time interval exceeds the reference interval.

30. A method of operating a DDI pacemaker, said pacemaker including means for sensing atrial depolarizations (P-waves) and ventricular depolarizations (R-waves), means for generating atrial stimulation pulses (A-pulses) and ventricular stimulation pulses (V-pulses), and means for defining a plurality of time intervals, periods or delays, said method comprising the steps of:

generating a pacing cycle that begins upon the occurrence of a ventricular event and terminates upon the occurrence of a successive ventricular event, where a ventricular event comprises either the sensing of an R-wave or the generating of a V-pulse;

starting the timing out of an atrial escape interval (AEI) and a post-ventricular atrial refractory period (PVARP) at the beginning of each pacing cycle;

sensing whether a P-wave occurs after the end of the PVARP but prior to the end of the AEI, and if not, generating an A-pulse at the conclusion of the AEI, and if so, inhibiting the generation of an A-pulse at the conclusion of the AEI;

starting an A-V delay (AVD) upon the timing out of the AEI, with the AVD terminating upon the earliest occurrence of either the sensing of an R-wave or the timing out of the AVD;

determining if a given pacing cycle includes the sensing of a P-wave and the generation of a V-pulse, and if so, measuring the P-to-V interval between the sensed P-wave and the generated V-pulse;

comparing the measured P-to-V interval to a reference interval and generating a pacemaker medicated retrograde rhythm (PMRR) detect signal if the measured P-to-V interval is greater than the reference interval;

extending the PVARP to an extended PVARP in the pacing cycle that begins following the generation of a PMRR detect signal; and determining if a P-wave is sensed during an alert period, $T_{ALERT}$, that begins at the end of the extended PVARP and concludes at the timing out of the AEI, and if not, generating an A-pulse at the timing out of the AEI.

31. The method as set forth in claim 30, further including selectively extending said AEI by an amount $T_F$ sufficient to assure that at least a prescribed time interval elapses between the sensing of a first P-wave within the pacing cycle and the generation of an A-pulse at the end of the AEI, said prescribed time interval comprising a time period sufficiently long to be greater than a natural refractory period following said first P-wave, whereby the A-pulse generated at the timing out of the extended AEI is assured of pacing at a nonrefractory time.

* * * * *